(12) United States Patent
Adami et al.

(10) Patent No.: US 8,153,370 B2
(45) Date of Patent: Apr. 10, 2012

(54) RNA FROM CYTOLOGY SAMPLES TO DIAGNOSE DISEASE

(75) Inventors: Guy Richard Adami, Brookfield, IL (US); Joel L. Schwartz, Chicago, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 358 days.

(21) Appl. No.: 12/407,604

(22) Filed: Mar. 19, 2009

(65) Prior Publication Data
US 2009/0239231 A1 Sep. 24, 2009

Related U.S. Application Data

(60) Provisional application No. 61/037,767, filed on Mar. 19, 2008.

(51) Int. Cl.
*C12Q 1/68* (2006.01)
*C12P 19/34* (2006.01)

(52) U.S. Cl. .................. 435/6.1; 435/6.11; 435/6.12

(58) Field of Classification Search .................. None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 6,171,785 B1 | 1/2001 | Higuchi | |
| 2009/0047667 A1* | 2/2009 | Wong .............................. | 435/6 |

FOREIGN PATENT DOCUMENTS

WO 2008051374 5/2008

OTHER PUBLICATIONS

Luo et al., "Human papillomavirus in oral squamous cell carcinoma and pre-cancerous lesions detected by PCR-based gene-chip array," Int. J. Oral. Maxillofac. Surg., 2007, vol. 36, pp. 153-158.*
Keshava et al., "Chlorophyllin significantly reduces benzo[a]pyrene [BP]-DNA adduct formation and alters Cytochrome P450 1A1 and 1B1 expression and EROD activity in normal human mammary epithelial cells (NHMECs)," Environ. Mol. Mutagen.., 2009, vol. 50, No. 2, pp. 134-144.*
Bhattacharyya et al., "Expression of Major Histocompatibility Complex (Class 1) in Premalignant and Malignant Epithelium", Oral Surgery Oral Medicine Oral Pathology, vol. 82, No. 2 Abstract, Aug. 1996.
Bicknell et al., "?2-Microglobulin Gene Mutations: A Study of Established Colorectal Cell Lines and Fresh Tumors", Proc. Natl. Acad. Sci. USA, vol. 91, pp. 4751-4755, 1994.
D'Urso et al., "Lack of HLA Class I Antigen Expression by Cultured Melanoma Cells FO-1 Due to a Defect in B2m Gene Expression", J. Clin. Invest., vol. 87, pp. 284-292, 1991.
Rosa et al., "The ?2-Microglobulin mRNA in Human Daudi Cells has a Mutated Initiation Codon but is Still Inducible by Interferon", The EMBO Journal, vol. 2, pp. 239-243, 1983.
Silvia et al., "Alteration of Serum Beta 2-Microglobulin in Oral Carcinoma", Indian Journal of Clinical Biochemistry, vol. 2, pp. 104-107, 2002.
Wen et al., "Preferential Induction of CYP1B1 by Benzo[?]pyrene in Human Oral Epithelial Cells: Impact on DNA Adduct Formation and Prevention By Polyphenols", Carcinogenesis, vol. 26, pp. 1774-1781, 2005.
Whipple et al., "A Genomic Predictor of Oral Squamous Cell Carcinoma", The Laryngoscope, vol. 114, pp. 1346-1354, 2004.

* cited by examiner

*Primary Examiner* — Young J Kim
(74) *Attorney, Agent, or Firm* — Nutter McClennen & Fish LLP; Thomas J. Engellenner

(57) ABSTRACT

The invention relates to methods and kits for detecting the likelihood that a subject has cancer, e.g., squamous cell carcinoma, by assaying the expression levels of tumor associated genes. More specifically, the expression levels of nucleic acids or proteins can be assayed in the tumor associated genes, e.g., beta-2 microgobulin (B2M) and cytochrome p450 1B1 (CYP1B1). The expression levels compared to standards can be indicative of the likelihood a subject has squamous cell carcinoma. For example, over-expression of B2M and under-expression of CYP1B1 can be indicative of the likelihood a subject has squamous cell carcinoma. Also, over-expression of B2M and over-expression of CYP1B1 can be indicative of the likelihood a subject has a precancerous squamous cell disorder. The expression levels of B2M and CYP1B1 can also be repeatedly assayed to monitor the progression of a squamous cell neoplasia.

7 Claims, 20 Drawing Sheets

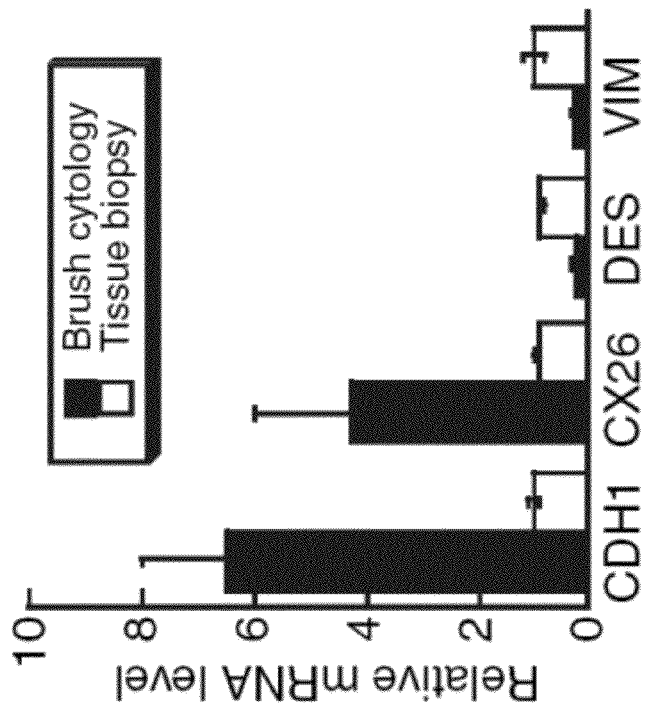
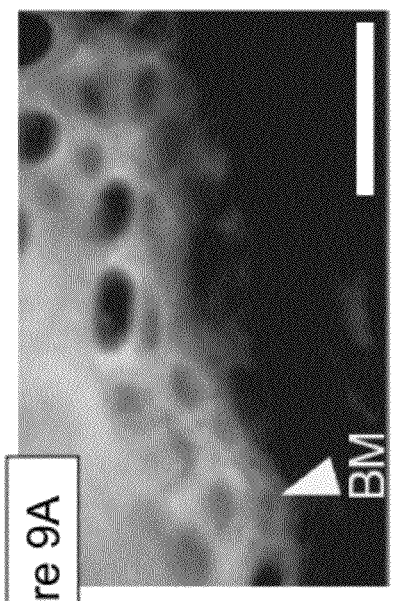
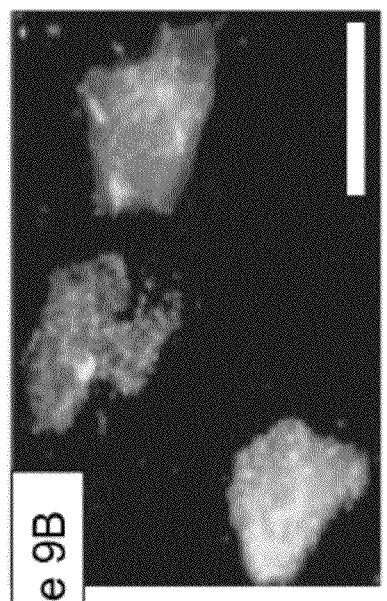
Figure 9A
Figure 9B
Figure 9C

RNA FROM CYTOLOGY SAMPLES TO DIAGNOSE DISEASE

RELATED APPLICATIONS

This application claims the benefit of U.S. Provisional Patent Application Ser. No. 61/037,767, filed Mar. 19, 2008, entitled "RNA From Cytology Samples to Diagnose Disease" which is herein incorporated by reference.

STATEMENT REGARDING FEDERALLY SPONSORED RESEARCH OR DEVELOPMENT

This invention was made with government support under NIH Grant No. CA085529 awarded by The National Cancer Institute. The government has certain rights in the invention.

FIELD OF THE INVENTION

The invention relates to methods and kits for detecting the likelihood that a subject has squamous cell carcinoma or neoplasia.

BACKGROUND OF THE INVENTION

Oral cancer can be any cancerous growth that is found in the mouth. It can arise as a primary lesion originating from any of the oral tissues. The most common form of oral cancer is oral squamous cell carcinoma, originating from the tissues that line the mouth and lips. Most oral cancers are malignant and can spread rapidly. In 2008, in the US alone, more than about 34,000 individuals will be diagnosed with oral cancer. Of these, 66% will be diagnosed with late stage three or four disease.

RNA expression analysis of oral keratinocytes can be used to detect early stages of disease such as oral cancer or to monitor on-going treatment responses of the same or other oral diseases. A limitation is the inability to obtain high quality RNA from oral tissue without using biopsies. While oral cytology cell samples can be obtained from patients in a minimally invasive manner they have not been validated for quantitative analysis of RNA expression.

Obtaining patient RNA without surgery would be an ideal way to facilitate large-scale genetic studies of cancer and simplify patient diagnosis. Because of the accessibility of the oral and cervical mucosa, methods have been in place for some time to examine histologic and genetic variations in normal and tumors cells. Very recently, methods to analyze RNA from cells and fluids from these organs have been explored. Establishing the validity of these approaches for quantification of gene expression remains an important goal.

Analysis of RNA in urine and saliva has the advantage of ease of use for marker discovery, but it has limitations because it does not provide a direct measure of gene expression in the tissue. It measures RNAs that are stable extracellularly, identifying markers that correlate with disease but are less likely to be informative about disease etiology. Potential problems exist. For example, the unknown contribution of RNA from dead and dying cells may not be readily assessed. Also, subtle differences in investigator sampling can accentuate differences in numbers and types of cells isolated.

Accordingly, there exists a need for better methods and kits for detecting the likelihood that a subject has squamous cell carcinoma or neoplasia. Accurate assay techniques for detecting or monitoring such disease states without resort to surgical biopsies would satisfy a long-felt need in the art.

SUMMARY OF THE INVENTION

Methods and kits are disclosed for detecting the likelihood that a subject has cancer, e.g., squamous cell carcinoma, by assaying the expression levels of tumor associated genes. More specifically, the expression levels of nucleic acids or proteins can be assayed in the tumor associated genes, e.g., beta-2 microgobulin (B2M) and cytochrome p450 1B1 (CYP1B1). The expression levels compared to standards can be indicative of the likelihood a subject has squamous cell carcinoma. For example, over-expression of B2M and under-expression of CYP1B1 can be indicative of the likelihood a subject has oral squamous cell carcinoma. Also, over-expression of B2M and over-expression of CYP1B1 can be indicative of the likelihood a subject has a precancerous oral squamous cell disorder. The expression levels of B2M and CYP1B1 can also be repeatedly assayed to monitor the progression of an squamous cell neoplasia.

In one aspect of the invention, a method for detecting the likelihood that a subject has squamous cell carcinoma comprises obtaining a brush cytology sample from a subject, extracting nucleic acids from cells in the sample, and assaying the nucleic acids for expression levels of non-degraded nucleic acid sequences coding for production of beta-2 microgobulin (B2M) and cytochrome p450 1B1 (CYP1B1), wherein over-expression of the B2M gene compared to a standard, together with under-expression of the CYP1B1 gene compared to a second standard is indicative of a likelihood that the subject has squamous cell carcinoma.

In another aspect of the invention brush cytology sampling is used to obtain squamous cells suitable for assays. The brush cytology instrument or brush can have one or two cutting surfaces. Brushes with one surface can comprise a rod with perpendicular bristles. Brushes with two surfaces can comprise a flat end of the brush and a circular border of the brush. Either surface can be used to obtain the specimen. To obtain the brush cytology sample, firm pressure with a brush can be applied to the area to be sampled. In some embodiments, a brush can be rotated in at least 20 brush strokes, where a single brush stroke is a forward to backward/backward to forward, a side to side or circular movement to obtain the sample. In some other embodiments, a first brush can be rotated in two to five brush strokes, to prime the surface by removing external dead or dying cells and expose underlying layers, then the first brush is discarded. Then a second brush can be rotated in the same location in at least 20 brush strokes to obtain the sample.

In one embodiment of the invention, the method further comprises amplifying and quantifying expression of the B2M gene and the CYP1B1 genes by real time polymerase chain reaction (q-PCR) using primers complementary to an mRNA sequence of at least 15 bases found at least 500 basepairs and preferably at least 1000 basepairs from the encoded 3' ends of the B2M and CYP1B1 mRNA transcripts. Amplifying expression products at least 500 basepairs and preferably at least 1000 basepairs from the encoded 3' ends of the transcripts, corresponding to the transcriptional start site, substantially full length and non-degraded nucleic acid sequences capable of producing proteins of increase, e.g., beta-2 microgobulin (B2M) or cytochrome p450 1B1 (CYP1B1), can be detected. Typically, non-degraded nucleic acid sequences are extracted from living cells taken as part of the sample. In contrast, degraded nucleic acid sequences are typically extracted from dead cells or cells undergoing apoptosis.

In another aspect, the invention is directed to a method for detecting the likelihood that a subject has squamous cell carcinoma, comprising detecting beta-2 microgobulin (B2M) and cytochrome p450 1B1 (CYP1B1) protein or nucleic acid expression levels in a sample from the subject, wherein over-expression of the B2M gene compared to a standard together with under-expression of the CYP1B1 gene compared to a second standard is indicative of a likelihood that the subject has oral squamous cell carcinoma. Moreover, another aspect of the invention is directed to detecting the likelihood that a subject has a precancerous squamous cell disorder, comprising detecting beta-2 microgobulin (B2M) and cytochrome p450 1B1 (CYP1B1) protein or nucleic acid expression levels in a sample from the subject, wherein over-expression of the B2M gene compared to a standard together with over-expression of the CYP1B1 gene compared to a second standard is indicative of a likelihood that the subject has a precancerous oral squamous cell disorder.

In one aspect, a method for monitoring squamous cell neoplasia in a human subject over time, comprising obtaining a brush cytology sample from a subject at a first time, extracting nucleic acids from cells in the sample, assaying said nucleic acids for the expression level of genes coding for the production of beta-2 microgobulin (B2M) and cytochrome p450 1B1 (CYP1B1), and repeating the steps of obtaining a sample, extracting nucleic acids and assaying for expression levels of B2M and CYP1B1 at a later time, wherein increased expression of the B2M gene at a later time or decreased expression of the CYP1B1 gene at a later time is indicative of progression of neoplasia. In one embodiment, squamous cell neoplasia in a human subject can be monitored over time in response to a treatment. A sample can be obtained, nucleic acids extracted from the sample, expression level of genes encoding for beta-2 microgobulin (B2M) and cytochrome p450 1B1 (CYP1B1) can be assayed, a treatment can be administered, wherein the treatment is a bioactive agent that inhibits cytochrome p450 proteins, sampling from the subject can be repeated over time and the expression level of B2M and CYP1B1 at a later time is indicative of the response to the treatment.

In yet another aspect, the invention is directed to a kit for assessing the presence of cancer in a sample comprising a pair of primers which specifically hybridize to at least one non-degraded nucleic acid sequences coding for production of beta-2 microglobulin (B2M) gene product or a cytochrome p450 1B1 (CYP1B1) gene product and reagents for real-time polymerase chain reaction (q-PCR). In additional embodiments, the kit can comprise additional tools, reagents or instruction manuals. For example, the kit can comprise a brush for obtaining a brush cytology sample from a subject. Also, the kit can comprise a nucleic acid extraction reagent to isolate nucleic acids from a sample.

Further understanding of various aspects of the invention can be obtained by reference to the following detailed description in conjunction with the associated drawings, which are described briefly below.

BRIEF DESCRIPTION OF THE DRAWINGS

FIG. 9A depicts a brush oral cytology immunofluorescent staining of a mucosal biopsy sample showed cytokeratin staining specifically in the cells of the epithelium (bar=10 lm, BM is basement membrane);

FIG. 9B depicts a brush cytology sample cells were highly enriched for cytokeratin staining; and FIG. 9C shows that brush cytology sample RNA was enriched for epithelial markers CDH1 and CX-26) and depressed for non-epithelial cell markers (DES and VIM) vs. the biopsy sample RNA. RNA was from five control hamsters.

DETAILED DESCRIPTION OF THE INVENTION

Figure 1:
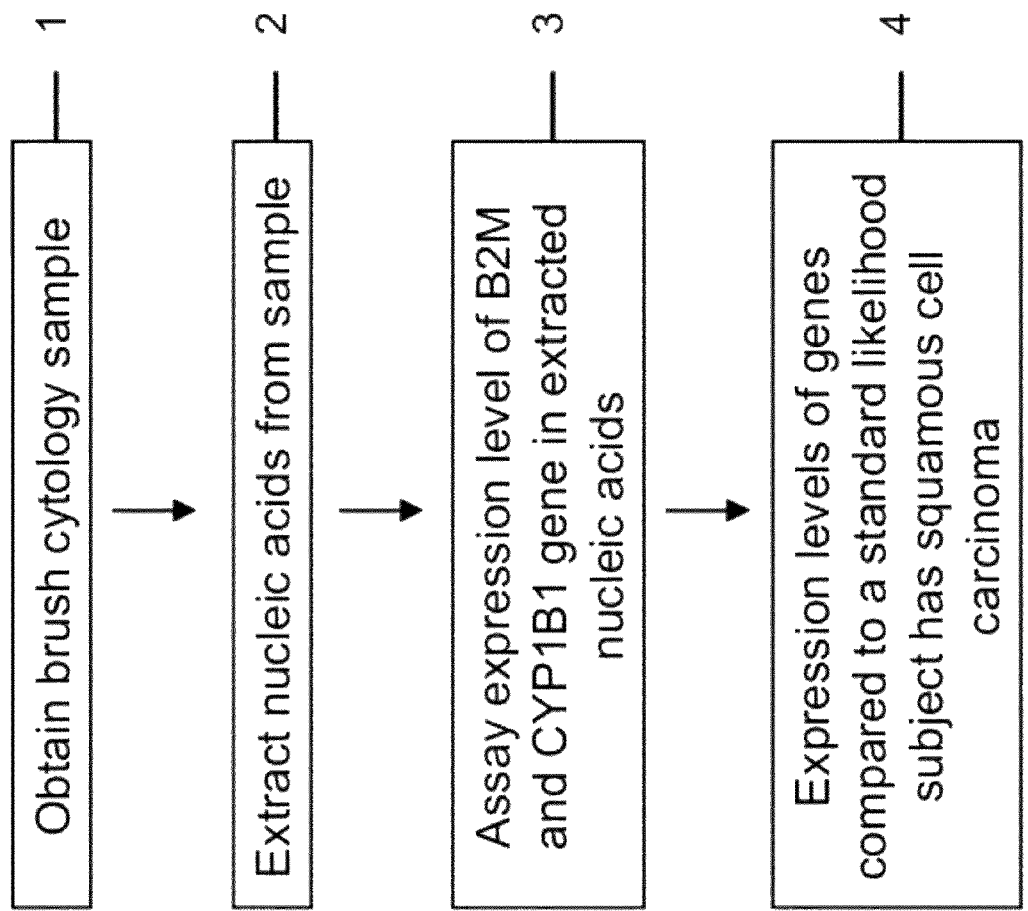
FIG. 1 is a flow chart depicting various steps in an embodiment of a method of the invention to detect the likelihood a subject has oral squamous cell carcinoma.

RNA analysis from brush oral cytology, on the other hand, has the advantage that live cells can be isolated from a site at risk for a disease such as oral squamous cell carcinoma (OSCC). Early changes in the disease progression that effect gene expression can be detected and because of the minimal invasiveness, the assay can be carried out repeatedly.

Pilot studies from the literature demonstrate that the isolation of RNA from brush oral cytology is possible and that mRNA can be detected using q-PCR or microarray analysis, but it is not clear how reliable the method is and what is being measured. One study indicated that 10-20% of the oral brush cytology mucosal cells from humans were viable as isolated, while we saw somewhat higher numbers from hamsters. In their human study, Spivack et al. saw a qualitative correlation of the detectability of expression of a number of mRNAs in laser microdissected lung tissue and brush cytology cells from the same patients. However, large inter-patient variability in mRNA quantitation was seen (up to 10000-fold) and the source of this variation was not explored. In another pilot study, RNAs from brush cytology cervical cells were compared to those from a surgically removed cervical tissue specimen by DNA microarray analysis, revealing that similar groups of genes were expressed above background.

The present invention relates, in part, to newly discovered correlations between the expression of selected genes, in particular, beta-2 microglobulin (B2M) and cytochrome p450 1B1 (CYP1B1) and the presence of cancer, such as, squamous cell carcinoma, in a subject. The relative expression level of the genes, e.g., B2M and CYP1B1, has been found to be indicative of squamous cell carcinoma in the subject and/or diagnostic of the presence or potential presence of squamous cell carcinoma in a subject. The invention features methods for detecting the likelihood a subject has squamous cell carcinoma, and methods of detecting the likelihood a subject has a precancerous squamous cell disorder by assaying nucleic acids for relative expression levels of B2M and CYP1B1 genes as compared to a standard.

The invention is also based, at least in part, on the identification of genes which are differentially expressed in samples from squamous carcinoma cells compared to non-cancer cells. A panel of known genes was screened for differential expression patterns in oral brush cytology samples (see Examples 1 and 2). Those genes with statistically significant ($p<0.01$) differences between the diseased and normal tissues were identified. This differential expression was observed either as a decrease in expression, or an increase in expression.

Accordingly, the present invention pertains to the analysis of B2M and/or CYP1B1 genes, the corresponding mRNA transcripts, and the encoded polypeptides, as an indication for the presence of or risk for development of, and the progression of squamous cell carcinoma. Overexpression of the B2M gene can be indicative of the presence of disease and a precancerous oral squamous cell disorder. Overexpression of the CYP1B1 gene can also be indicative of the likelihood a subject has a precancerous oral squamous cell disorder, while the underexpression of the CYP1B1 gene can be indicative the subject has oral squamous cell carcinoma.

Detection of the presence or expression levels of non-degraded nucleic acid sequences, e.g., at least 500 basepairs and preferably at least 1000 basepairs from the encoded 3' ends of the B2M or CYP1B1 mRNA transcripts, in nucleic acids can be performed using methods known in the art. Typically, it can be convenient to assess the presence and/or quantity of MRNA or CDNA by real-time polymerase chain reaction (q-PCR) or quantitative-PCR (q-PCR), in which mRNA can be isolated from a cell or tissue sample, converted to cDNA using reverse transcriptase by methods known in the art, hybridized with gene specific oligonucleotides (e.g., B2M or CYP1B1 primers), and amplified in the presence of probe or diagnostic label. The label group can be a fluorescent compound. Other useful methods of mRNA detection and/or quantification include northern blot, gel electrophoresis, column chromatography, q-PCR, and other methods known by one skilled in the art.

Figure 2:
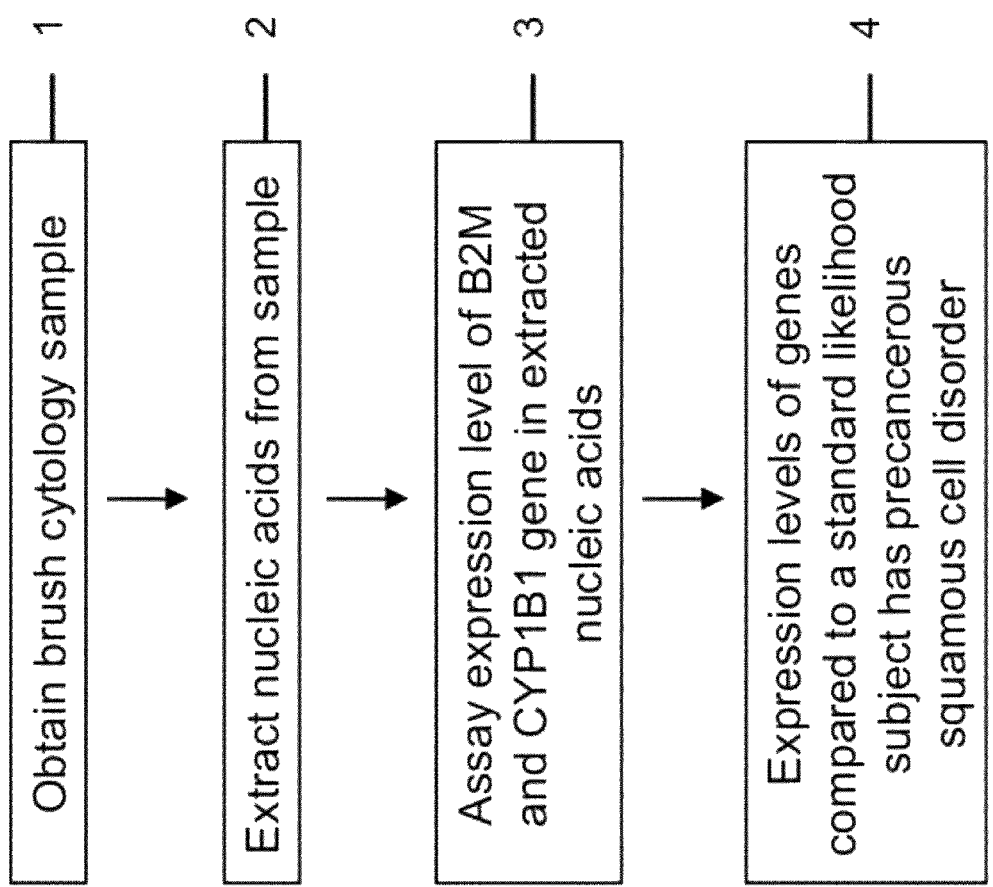
FIG. 2 is flow chart depicting various steps in an embodiment of a method of the invention to detect the likelihood a subject has a precancerous oral squamous cell disorder.

In another aspect, the invention provides a method for detecting the likelihood that a subject has squamous carcinoma by assaying expression level of B2M and CYP1B1 genes, whose quantity or expression level is assayed for the likelihood that a subject has squamous carcinoma (FIG. 1). The genes, e.g., B2M and CYP1B1, are either increased or decreased in expression level in the cancer tissue in a fashion that is either positively or negatively indicative of the subject having squamous cell carcinoma. In yet another aspect, the invention provides a method for detecting the likelihood that a subject has a precancerous squamous cell disorder by assaying the expression levels of B2M and CYP1B1 genes (FIG. 2). The genes are either increased or decreased in expression level that can be indicative that the subject has a precancerous squamous cell disorder.

Figure 3:
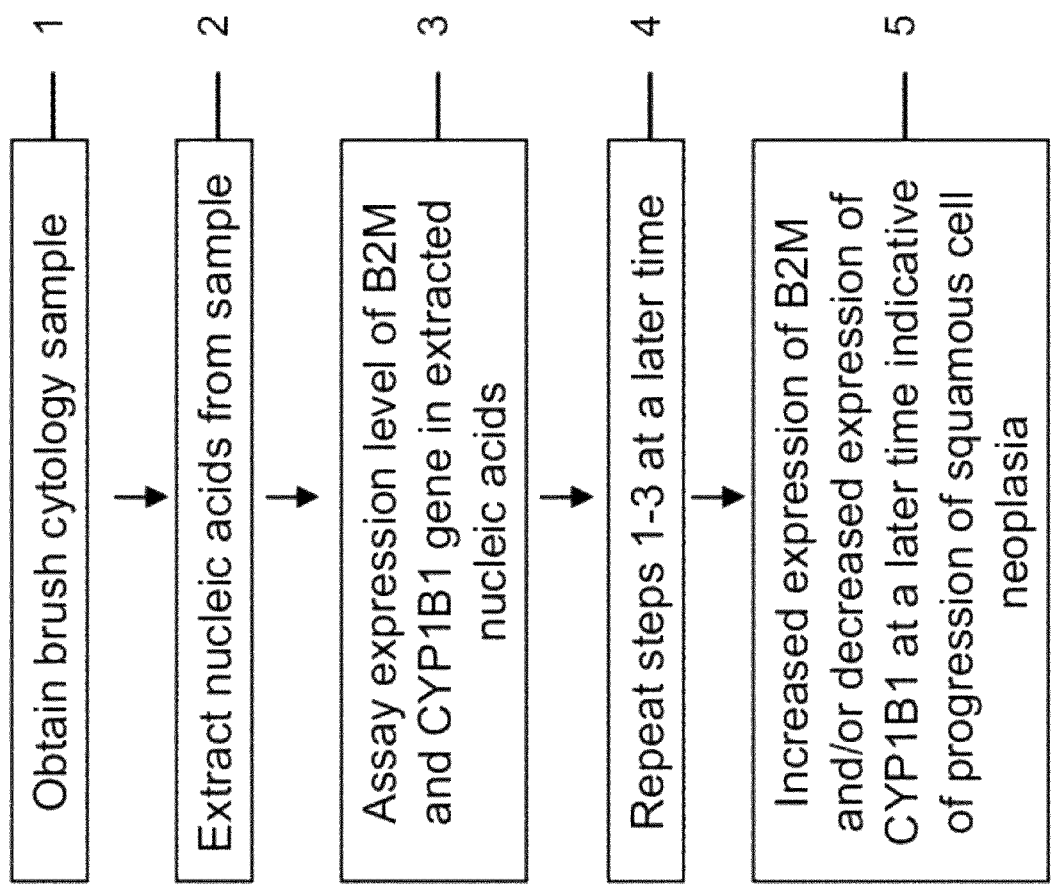
FIG. 3 is flow chart depicting various steps in an embodiment of a method of the invention to monitor the progression of an oral squamous cell neoplasia over time.

In yet another aspect, the invention provides a method for monitoring squamous cell neoplasia in a human subject over time by assaying the expression level of B2M and CYP1B1 genes, whose expression level is assayed for the likelihood that a subject has squamous carcinoma (FIG. 3).

The terms used in this invention adhere to the standard definitions generally accepted by those having ordinary skill in the art. In case any further explanation might be needed, some terms have been elucidated below and throughout the application.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules") in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

As used herein, the terms "polynucleotide," "oligonucleotide" and "nucleic acid sequences" are used interchangeably, and include polymeric forms of nucleotides of any length, either deoxyribonucleotides or ribonucleotides, or analogs thereof. Polynucleotides can have any three-dimensional structure, and can perform any function, known or unknown. The following are non-limiting examples of polynucleotides: a gene or gene fragment, exons, introns, messenger RNA (mRNA), transfer RNA, ribosomal RNA, ribozymes, complementary DNA (cDNA), recombinant polynucleotides, branched polynucleotides, plasmids, vectors, isolated DNA of any sequence, isolated RNA of any sequence, nucleic acid probes, and primers. A polynucleotide can comprise modified nucleotides, such as methylated nucleotides and nucleotide analogs. If present, modifications to the nucleotide structure can be imparted before or after assembly of the polymer. The sequence of nucleotides can be interrupted by non-nucleotide components. A polynucleotide can be further modified after polymerization, such as by conjugation with a labeling component. The term also includes both double- and single-stranded molecules. Unless otherwise specified or required, any embodiment of this invention that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for guanine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

A "gene" includes a polynucleotide containing at least one open reading frame that is capable of encoding a particular polypeptide or protein after being transcribed and translated. Any of the polynucleotide sequences described herein can be used to identify larger fragments or full-length coding sequences of the gene with which they are associated. Methods of isolating larger fragment sequences are known to those of skill in the art, some of which are described herein. Previously known and uncharacterized polymorphisms in beta-2 microgobulin (B2M) and cytochrome p450 1B1 (CYP1B1) genes are also included within this invention. In addition, alternative splicing products that produce variation in the mRNA expression pattern are also included.

A "gene product" includes an amino acid (e.g., peptide or polypeptide) generated when a gene is transcribed and translated.

The terms "tumor-associated genes" as used herein refers to a gene(s) found to be differentially expressed, either over-expressed or under-expressed in cancer tissue and originally identified by their differential expression in cancer cells compared to non-cancer cells.

The term "non-degraded" nucleic acid sequences as used herein refers to substantially full length nucleic acid sequences capable of producing proteins of interest, e.g., beta-2 microgobulin (B2M) or cytochrome p450 1B1 (CYP1B1). Typically, non-degraded nucleic acid sequences are extracted from living cells taken as part of the sample. In contrast, "degraded nucleic acid sequences" are typically extracted from dead cells or cells undergoing apoptosis. Amplifying expression products at least 500 basepairs and preferably at least 1000 basepairs from the encoded 3' ends of the mRNA transcripts, corresponding to the transcriptional start site, substantially full length and non-degraded nucleic acid sequences capable of producing proteins of increase, e.g., beta-2 microgobulin (B2M) or cytochrome p450 1B1 (CYP1B1), can be detected. Alternatively, non-degraded nucleic acid sequences preferable for the assay purposes disclosed herein are typically at least 50 percent or more of the full-length gene and suitable primers can be used to selectively amplify such nucleic acid sequences.

A "probe" when used in the context of polynucleotide manipulation includes a reagent to detect a target present in a sample of interest by hybridizing or incorporation with the target. Usually, a probe will comprise a label or a means by which a label can be attached or incorporated with the target. Suitable labels include, but are not limited to fluorochromes, chemiluminescent compounds, dyes, and proteins, including enzymes.

A "primer" includes a short polynucleotide, generally with a free 3'-OH group that binds to a target or "template" present in a sample of interest by hybridizing with the target, and thereafter promoting polymerization of a polynucleotide complementary to the target. A "polymerase chain reaction" ("PCR") is a reaction in which replicate copies are made of a target polynucleotide using a "pair of primers" or "set of primers" consisting of "upstream" and a "downstream" primer, and a catalyst of polymerization, such as a DNA polymerase, and typically a thermally-stable polymerase enzyme. Methods for PCR are well known in the art, and are taught, for example, in MacPherson et al., IRL Press at Oxford University Press (1991)). "Quantitative PCR" ("q-PCR"), also referred herein as real-time PCR (q-PCR), is based on PCR to amplify and simultaneously quantify a target DNA molecule. All processes of producing replicate copies of a polynucleotide, such as PCR or gene cloning, are collectively referred to herein as "replication". A primer can also be used as a probe in hybridization reactions, such as Southern or Northern blot analyses (see, e.g., Sambrook, J., Fritsh, E. F., and Maniatis, T. *Molecular Cloning: A Laboratory Manual*. 2nd, ed., Cold Spring Harbor Laboratory, Cold Spring Harbor Laboratory Press, Cold Spring Harbor, N.Y., 1989).

The term "cDNAs" includes complementary DNA, that is mRNA molecules present in a cell or organism generated into cDNA with an enzyme such as reverse transcriptase. A "cDNA library" includes a collection of MRNA molecules present in a cell or organism, converted into cDNA molecules with the enzyme reverse transcriptase, then inserted into "vectors" (other DNA molecules that can continue to replicate after addition of foreign DNA). Exemplary vectors for libraries include bacteriophage, viruses that infect bacteria (e.g., lambda phage). The library can then be probed for the specific cDNA (and thus mRNA) of interest.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence can usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences. Various splice acceptor sites can be necessary for RNA splicing and can be included herein within the definition of "control sequences." Some such sequences also play a role in the abundance and stage-specificity of gene expression.

As used herein, "expression" includes the process by which polynucleotides are transcribed into mRNA and translated into peptides, polypeptides, or proteins. If the polynucleotide is derived from genomic DNA, expression may include splicing of the mRNA, if an appropriate eukaryotic host is selected. Regulatory elements required for expression can include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG (Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989). Similarly, a eukaryotic expression vector can include a heterologous or homologous promoter for RNA polymerase II, a downstream polyadenylation signal, the start codon AUG, and a termination codon for detachment of the ribosome. Such vectors can be obtained commercially or assembled by the sequences described in methods well known in the art, for example, the methods described below for constructing vectors in general.

"Differentially expressed", as applied to a gene, includes the differential production of mRNA transcribed from a gene or a protein product encoded by the gene. A differentially expressed gene may be overexpressed or underexpressed as compared to the expression level of a normal, control cell or standard. In one aspect, it includes a differential that can be 1.5 times, preferably 2 times or preferably greater than 2 times higher or lower than the expression level detected in a control sample. The term "differentially expressed" can also include nucleotide sequences in a cell or tissue which are expressed where silent in a control cell or not expressed where expressed in a control cell.

The term "polypeptide" includes a compound of two or more subunit amino acids. The subunits can be linked by peptide bonds. In another embodiment, the subunit can be linked by other bonds, e.g., ester, ether, etc. As used herein the term "amino acid" includes either natural and/or unnatural or synthetic amino acids, including glycine and both the D or L optical isomers. A peptide of three or more amino acids can commonly be referred to as an oligopeptide. Peptide chains of greater than three or more amino acids can be referred to as a polypeptide or a protein.

"Hybridization" includes a reaction in which one or more polynucleotides react to form a complex that can be stabilized via hydrogen bonding between the bases of the nucleotide residues. The hydrogen bonding can occur by Watson-Crick base pairing, Hoogstein binding, or in any other sequence-specific manner. The complex can comprise two strands forming a duplex structure, three or more strands forming a multi-stranded complex, a single self-hybridizing strand, or any combination of these. A hybridization reaction can constitute a step in a more extensive process, such as the initiation of a PCR reaction, or the enzymatic cleavage of a polynucleotide by a ribozyme.

A nucleic acid molecule can be "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., 1989, supra). The conditions of temperature and ionic strength determine the "stringency" of the hybridization. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. Preferably a minimum length for a hybridizable nucleic acid can be at least about 10 nucleotides; more preferably at least about 15 nucleotides.

Hybridization reactions can be performed under conditions of different "stringency". The stringency of a hybridization reaction includes the difficulty with which any two nucleic acid molecules can hybridize to one another. Under stringent conditions, nucleic acid molecules at least 60%, 65%, 70%, 75% identical to each other remain hybridized to each other, whereas molecules with low percent identity cannot remain hybridized.

When hybridization occurs in an antiparallel configuration between two single-stranded polynucleotides, the reaction is called "annealing" and those polynucleotides are described as "complementary". A double-stranded polynucleotide can be "complementary" or "homologous" to another polynucleotide, if hybridization can occur between one of the strands of the first polynucleotide and the second. "Complementarity" or "homology" (the degree that one polynucleotide is complementary with another) is quantifiable in terms of the proportion of bases in opposing strands that are expected to hydrogen bond with each other, according to generally accepted base-pairing rules.

An "antibody" includes an immunoglobulin molecule capable of binding an epitope present on an antigen. As used herein, the term encompasses not only intact immunoglobulin molecules such as monoclonal and polyclonal antibodies, but also anti-idiotypic antibodies, mutants, fragments, fusion proteins, bi-specific antibodies, humanized proteins, and modifications of the immunoglobulin molecule that comprises an antigen recognition site of the required specificity.

The term "cancerous" as used herein is intended to refer to any abnormal cells that divide without control characterized by the proliferation of anaplastic cells that can invade surrounding tissues and metastasize to new body sites.

The term "oral cancer" as used herein refers to any cancerous tissue growth located in the mouth. It can arise as a primary lesion originating in any of the oral tissues, by metastasis from a distant site of origin, or by extension from a neighboring anatomic structure. Oral cancers can originate in any of the tissues of the mouth. The most common oral cancer is squamous cell carcinoma, originating in the tissues that line the mouth and lips. Oral or mouth cancer most commonly involves the tissue of the lips or the tongue. Oral cancer can also occur on the floor of the mouth, cheek lining, gingiva (gums), or the palate (roof of the mouth). Many oral cancers can be malignant and can spread rapidly. Oral cells can include, but are not limited to, pseudostratified epithelium, columnar epithelium and a variety of squamous epithelium: keratinized, non-keratinized and stratified.

The terms "squamous cell carcinoma" refer to a type of cancer that can occur in a variety of organs, including, but not limited to: lips, skin, mouth, nose, esophagus, urinary bladder, prostate, lungs, vagina and cervix.

The term "subject" refers to any living organism. The term subject comprises, but is not limited to, humans, nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered. In preferred embodiments, the subject is a mammal, including humans and non-human mammals. In a more preferred embodiment, the subject is a mammal. In the most preferred embodiment, the subject is a human.

The terms "sample," "sample from a subject" and "extracted sample" as used herein refer to a small quantity of tissue from a subject, which can be obtained, e.g., by employing methods known in the art. Such a tissue sample, e.g., brush cytology sample, can contain cancer cells, non-cancer cells or both. The term sample comprises, but is not limited to, oral tissues, oral cells from the mouth, lips, tongue, cheek lining, gingiva, palate, skin, nose, esophagus, urinary bladder, prostate, lungs, vagina and cervix of a subject.

The term "standard" as used herein refers to a control sample. The "standard" expression levels can be detected, for example, in non-cancer samples, normal subjects without cancer or untreated samples. The "standard" expression level can also refer to nucleic acid expression levels or protein levels present in non-cancer samples, normal subjects without cancer or untreated samples. Standards can provide a control or comparison for determining the outcome of the experiment. Internal "standard" refers to an experimental optimal control to determine the consistency of an experiment or set of experiments. An example of internal standards can be potential housekeeping genes identified on their constant expression in many tissues or on consistent levels in normal and tumor tissue.

Various aspects of the invention are described in further detail in the following subsections:

I. Beta-2 Microglobulin (B2M)

Beta-2 microglobulin (B2M) (NM_004048) (SEQ ID.: 1) is a component of the major histocompatibility complex (MHC) class 1 molecules, which are present on almost all nucleated cells of the body. B2M lies lateral to the alpha3 chain on the cell surface and lacks a transmembrane domain. It interacts with the alpha chains and class 1-like molecules, which are important for antigen presentation.

Beta-2-microglobulin has been found in the serum of normal individuals and in the urine in elevated amounts in patients with Wilson disease, cadmium poisoning, and other conditions leading to renal tubular dysfunction.

Previous studies have found that some tumors lack cell surface expression of HLA class 1 molecules and this can be one mechanism by which tumor cells escape immune recognition by cytotoxic T cells. In some cases, tumor escape is due to loss of the heavy chain surface expression encoded by the HLA-A, -B, and -C genes; in other cases, defects in expression of the B2M gene for the light chain can be responsible.

The Daudi lymphoblastoid cell line, derived from a patient with Burkitt lymphoma and lacking both HLA antigens and beta-2 microglobulin, fails to express HLA class 1 molecules because of a specific defect in the B2M component. In the human melanoma cell line FO-1, it was found that the lack of expression of HLA class 1 antigens was the result of a defect in the B2M gene: a deletion of the first exon of the 5-prime flanking region and of a segment of the first intron. Analyses using single-strand conformation polymorphism (SSCP) analysis to screen a series of 37 established colorectal cell lines, 22 fresh tumor samples, and 22 normal DNA samples for mutations in the B2M gene, found mutations in 6 of 7 colorectal cell lines and 1 of 22 fresh tumors, whereas no mutations were detected in the normal DNA samples. Sequencing of these mutations showed that an 8-bp CT repeat in the leader peptide sequence was particularly variable, since 3 of the cell lines and 1 fresh tumor sample had deletions in this region. In 2 related colorectal cell lines, DLD-1 and HCT-15, 2 similar mutations were identified. Expression of beta-2-microglobulin was examined using a series of monoclonal antibodies in an ELISA system and reduced expression was correlated with a mutation in 1 allele of the B2M gene, whereas loss of expression was seen in instances where a line was homozygous for a mutation or heterozygous for 2 mutations.

Figure 4:
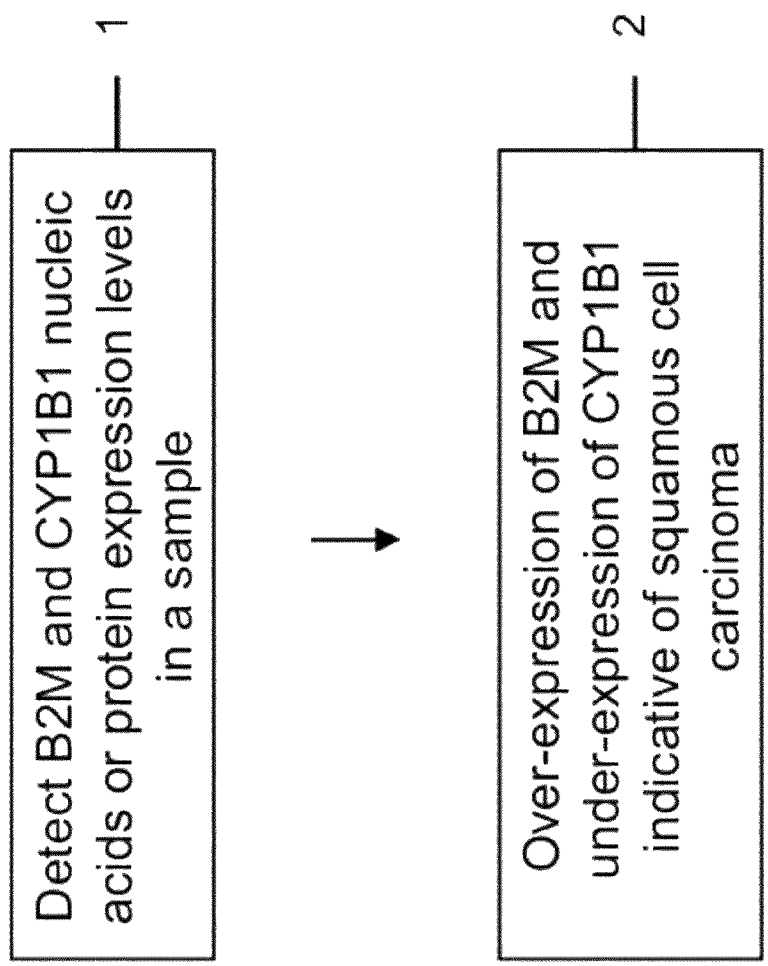
FIG. 4 is flow chart depicting various steps in an exemplary embodiment of a method of the invention to detect the likelihood a subject has oral squamous cell carcinoma.
Figure 5:
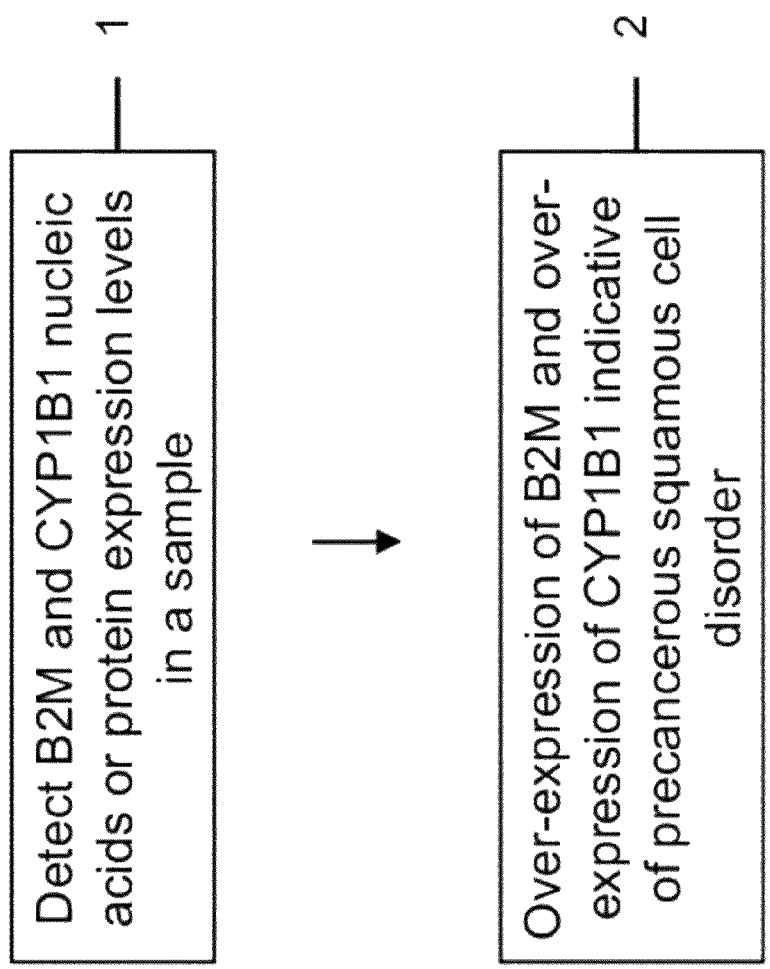
FIG. 5 is flow chart depicting various steps in an exemplary embodiment of a method of the invention to detect the likelihood a subject has a precancerous oral squamous cell disorder.

The present invention provides, in part, a method to detect expression level changes in tumor-associated genes, such as changes in B2M gene expression levels, in brush cytology samples. In one aspect of the invention, the nucleic acid expression level, e.g., increased expression, of the B2M gene is indicative of a likelihood that a subject has squamous cell carcinoma (FIG. 1). In another aspect of the invention, protein or nucleic acid expression level, e.g., increased expression, of B2M is compared to a standard and is indicative of a likelihood that the subject has squamous cell carcinoma (FIG. 4). In yet another aspect of the invention, protein or nucleic acid expression levels, e.g., increased expression, of the B2M gene compared to a standard is indicative of a likelihood that the subject has a precancerous squamous cell disorder (FIG. 5). In one aspect of the invention, nucleic acids expression level of B2M is assayed over time, at repeated intervals, and expression level, e.g., increased expression, of the B2M gene is indicative of progression of neoplasia (FIG. 3). In another aspect of the invention, nucleic acids expression level of B2M is compared to a standard and over-expression of B2M is indicative of a likelihood that the subject has a precancerous squamous cell disorder (FIG. 2). In yet another aspect of the invention, a kit is provided for assessing the presence of cancer in a sample comprising a pair of primers that specifically hybridize to at least one non-degraded B2M nucleic acid sequences and reagents for real-time PCR.

II. Cytochrome P450 Proteins

Cytochrome p450 proteins are a large and diverse family of hemoproteins and monooxygenases which catalyze reactions involved in drug metabolism and synthesis of cholesterol, steroids and other lipids and responsible for the phase 1 metabolism of a wide range of structurally diverse substrates by inserting 1 atom of atmospheric oxygen into the substrate molecule, thereby creating a new functional group (e.g., —OH, —NH2, —COOH). Some well known family members include: cytochrome p450 and cytochrome p450 1A1 (CYP1A1). While less studied and more recently discovered, cytochrome p450 1B1 (CYP1B1) (NM_000104)(SEQ ID.: 2) also belongs to the cytochrome 450 superfamily of proteins. CYP1B1 was originally identified in 1994 through its homology to other identified family members, such as CYP1A1 with 44% identity. Despite the similarity, the two enzymes have very different catalytic efficiencies and metabolites when incubated with common substrates. CYP1B1 has also been found to be regulated by the aryl hydrocarbon receptor, a ligand activated transcription factor, and is expressed in many normal human tissues.

Recently CYP1B1 has been shown to be important in fetal development, with mutations linked to a form of primary congenital glaucoma. Screening for the presence of coding sequence changes in the CYP1B1 gene identified 3 different truncating mutations: a 13-bp deletion found in 1 consanguineous and 1 nonconsanguineous family; a single cytosine insertion observed in another 2 consanguineous families; and a large deletion found in an additional consanguineous family. In addition, a G-to-C transversion at nucleotide 1640 of the CYP1B1 coding sequence was found that caused a val432-to-leu amino acid substitution. This change created an EcoR57 restriction site, thus providing a rapid screening method. Heterozygosity for the val432-to-leu change was found in 51.4% of 70 normal individuals. This amino acid change was not in that part of CYP1B1 that represented conserved sequences, and both valine and leucine are neutral and hydrophobic. Their very similar aliphatic side groups differ by a single —CH2 group. Therefore, this change appeared to represent a common amino acid polymorphism that is not related to the primary congenital glaucoma phenotype. However the finding was not unexpected, as a link between members of this superfamily and the processes of growth and differentiation had been postulated previously. They speculated that CYP1B1 participates in the metabolism of an as-yet-unknown biologically active molecule that is a participant in eye development.

The present invention generally provides a method that detects tumor-associated changes in the expression level in genes, such as changes in CYP1B1 expression levels, in brush cytology samples. In one aspect of the invention, the nucleic acid expression level, e.g., decreased expression, of the CYP1B1 gene is indicative of a likelihood that a subject has squamous cell carcinoma (FIG. 1). In another aspect of the invention, protein or nucleic acid expression level, e.g., decreased expression, of CYP1B1 is compared to a standard and is indicative of a likelihood that the subject has squamous cell carcinoma (FIG. 4). In yet another aspect of the invention, protein or nucleic acid expression levels, e.g., increased expression, of the CYP1B1 gene compared to a standard is indicative of a likelihood that the subject has a precancerous squamous cell disorder (FIG. 5). In one aspect of the invention, nucleic acid expression level of CYP1B1 can be monitored over time, at repeated intervals, and the expression level, e.g., decreased expression, of the CYP1B1 gene is indicative of progression of squamous cell neoplasia (FIG. 3). In another aspect of the invention, nucleic acids expression level of CYP1B1 is compared to a standard and over-expression of CYP1B1 is indicative of a likelihood that the subject has a precancerous squamous cell disorder (FIG. 2). In yet another aspect of the invention, a kit is provided for assessing the presence of cancer in a sample comprising a pair of primers that specifically hybridize to at least one non-degraded CYP1B1 nucleic acid sequences and reagents for real-time RT-PCR.

Another aspect of the invention relates to inhibiting CYP1B1, and other cytochrome p450 family members, such as CYP1A1, as a method to inhibit carcinogenesis. Bioactive agents have been characterized to inhibit cytochrome p450-metabolism, and related family members-metabolism, of certain medications leading to increased bioavailability. Many of these bioactive agents are naturally occurring and can be found in grapefruit juice and other fruit juices. Some examples can include, but are not limited to, bergamottin, dihydroxybergamottin, geraniol and resveratrol (a phytoalexin). In another aspect of the invention, administering inhibitors of cytochrome p450 can be useful in treating or inhibiting squamous cell neoplasia. The inhibitors can be a bioactive agent that inhibits cytochrome p450 proteins and at least one of cytochrome p450 1B1 (CYP1B1), cytochrome p450 1A1 (CYP1A1) and combinations thereof.

III. Predictive Medicine

The present invention pertains to the field of predictive medicine in which diagnostic assays, prognostic assays, pharmacogenetics and monitoring clinical trials are used for prognostic (predictive) purposes to thereby detect a precancerous, cancerous or progression of a squamous cell cancer. Accordingly, one aspect of the present invention relates to diagnostic assays for detecting gene expression of nucleic acid and/or protein, in the context of a sample (e.g., brush cytology sample) to thereby detect the likelihood that a subject has a precancerous squamous cell disorder, has squamous cell carcinoma, or to monitor the progression of a squamous cell neoplasia, associated with increased or decreased nucleic acid and/or protein expression.

1. Harvesting the Sample

In one aspect of the invention, the sample can be a biopsy sample or a small number of cells or a tissue sample removed for processing. Common examples of biopsy methods can include, but are not limited to, brush cytology, core needle biopsy, surgical biopsy, punch biopsy, shave biopsy, incisional/excisional biopsy and curettage biopsy.

A brush cytology method can utilize a brush to obtain a complete transepithelial specimen with cellular representation from each of the three layers: the basal, intermediate, and superficial layers. Unlike some cytology instruments, which collect only exfoliated superficial cells, the brush cytology sample penetrates to the basement membrane, removing tissue from all three epithelial layers of the mucosa. The brush cytology can be performed with or without topical or local anesthetic. The brush cytology instrument or brush can have one or two cutting surfaces. Brushes with one surface can comprise a rod with perpendicular bristles. Brushes with two surfaces can comprise a flat end of the brush and a circular border of the brush. Either surface can be used to obtain the specimen.

Brush cytology samples can be utilized to routinely detect precancerous disorders and carcinomas. The diagnosis of a cancer can be, accordingly, made when a lesion is suspicious enough that it causes a health practitioner or other person skilled in the art to refer the lesion for further analysis. Thus, the brush cytology can be a method of detecting a precancerous squamous cell disorder, which can prevent the cancer from developing further, and it can be a method of identifying unsuspected cancers at early and treatable stages.

The brush cytology sample can provide a health practitioner or other person skilled in the art with a diagnostic screening test. In one aspect of the invention, a brush cytology sample can be obtained. Prior to obtaining the sample, it is preferable to rinse the subjects mouth with physiologic saline (pH 7.4) to remove any foreign debris that can be collected during the sample harvest. The mouth rinse can be saline solution or any commercially available mouth wash. Firm pressure with a brush can be applied to the area to be sampled. In some embodiments, a brush can be rotated in at least 20 brush strokes, where a single brush stroke is a forward to backward/backward to forward, a side to side or circular movement to obtain the sample. In some other embodiments, a first brush can be rotated in two to five brush strokes, to prime the surface, then the first brush is discarded. Then a second brush can be rotated in the same location in at least 20 brush strokes to obtain the sample. Little to no bleeding should result after the sample harvest. In another embodiment, the brush cytology sample can comprise squamous cells.

2. Diagnostic Assays

An exemplary method for detecting the presence or absence of nucleic acid or protein of the invention in a biological sample involves obtaining a sample from a subject, e.g., brush cytology sample, assaying the expression level (e.g., mRNA, cDNA or protein) of genes (e.g., B2M and CYP1B1) and comparing the expression levels to a standard to detect the likelihood the subject has a precancerous squamous cell disorder, squamous cell carcinoma or to monitor the progression of a neoplasia. A preferred method for detecting expression level of messenger ribonucleic acid (mRNA) or complementary deoxyribonucleic acid (cDNA) can use amplification and quantification of specific nucleic acids. Such polymerase chain reaction (PCR) methods can be referred to as: quantitative PCR (q-PCR), real-time PCR (q-PCR) and quantitative real-time PCR, see also U.S. Pat.

No. 6,171,785, which can be modified and adapted for use by methods known to those of ordinary skill in the art.

Primers based on the nucleotide sequence of the genes of the invention can be used to detect transcripts corresponding to the gene(s) of the invention. In some embodiments, a primer pair can be designed by utilizing primer design software, such as GenScript, Primer3, PRIDE and Primer Express. Commercial primers are also available for purchase corresponding to multiple locations throughout the gene. In an exemplary embodiment, the primers can be complementary to an mRNA sequence of at least 15 bases found at least 500 basepairs and preferably at least 1000 basepairs from the encoded 3' ends of the transcripts, corresponding to the transcriptional start site. By specifying at least 500 basepairs and preferably at least 1000 basepairs from the encoded 3' ends of the transcripts for amplification, the q-PCR can be biased toward detecting the expression levels of non-degraded mRNA without interference of degraded mRNA that can be extracted from dead cells or cells undergoing apoptosis.

Another embodiment for detecting RNA or DNA corresponding to a gene or protein of the invention can be with the use of a labeled nucleic acid probe capable of hybridizing to a mRNA or cDNA of the invention. A wide variety of conventional techniques are available, including mass spectrometry, chromatographic separations, 2-D gel separations, binding assays (e.g., immunoassays), competitive inhibition assays, one- and two-dimensional gels and sandwiched ELISA. Typical methodologies for RNA detection include RNA extraction from a cell or tissue sample, followed by hybridization of a labeled probe, (e.g., a complementary polynucleotide) specific for the target RNA to the extracted RNA, and detection of the probe (e.g., Northern blotting), direct sequencing, gel electrophoresis, column chromatography, and quantitative PCR.

The term "sample" is intended to include tissues, cells and biological samples isolated from a subject (e.g., brush cytology sample), as well as tissues, cells and fluids present within a subject. That is, the detection method of the invention can be used to detect mRNA, protein, or cDNA in a sample in vitro as well as mRNA or protein in vivo. For example, in vitro techniques for detection of mRNA can include PCR, q-PCR, northern hybridizations and in situ hybridizations. In vitro techniques for detection of protein can include enzyme linked immunosorbent assays (ELISAs), western blots, immunoprecipitations and immunofluorescence. In vitro techniques for detection of cDNA can include Southern hybridizations, PCR, q-PCR. Furthermore, in vivo techniques for detection of protein can include introducing into a subject a labeled antibody. For example, the antibody can be labeled with a radioactive label whose presence and location in a subject can be detected by standard imaging techniques.

In one aspect of the invention, methods for detecting the likelihood that a subject has squamous cell carcinoma can involve obtaining a sample (e.g., brush cytology sample) from a subject, extracting nucleic acids from the sample, mRNA, or generating to cDNA from mRNA, assaying the nucleic assaying the nucleic acids for expression level of non-degraded nucleic acid sequences coding for production of beta-2 microgobulin (B2M) and cytochrome p450 1B1 (CYP1B1) and wherein over-expression of the B2M gene compared to a standard, together with under-expression of the CYP1B1 gene compared to a second standard is indicative of a likelihood that the subject has squamous cell carcinoma. Examples of a standard can be, but are not limited to, a non-cancer cells sample, brush cytology sample from a control subject and normal cells.

In another aspect of the invention, the methods can involve obtaining a control sample (e.g., non-cancer cells sample) from a subject, extracting nucleic acids from the sample, mRNA, or generating to cDNA from mRNA, assaying the nucleic acids for expression level of non-degraded nucleic acid sequences coding for production of beta-2 microgobulin (B2M) and cytochrome p450 1B1 (CYP1B1) and wherein over-expression of the B2M gene compared to a standard together with over-expression of the CYP1B1 gene compared to a second standard is indicative of a likelihood that the subject has a precancerous squamous cell disorder.

The invention also encompasses kits for detecting the presence of expression of the genes, B2M and CYP1B1, in a sample. For example, the kit can comprise a pair of primers which specifically hybridize to at least one non-degraded nucleic acid sequences coding for production of beta-2 microglobulin (B2M) gene or a cytochrome p450 1B1 (CYP1B1) gene and reagents for real-time polyrnerase chain reaction (q-PCR). The kit can further comprise a brush to obtain a brush cytology sample and nucleic acid extraction reagents. Furthermore, the kit can comprise instructions for using the kit to detect protein or nucleic acids.

In certain embodiments, detection of the expression levels can involve the use of a probe/primer in a polymerase chain reaction (PCR) (see, e.g., U.S. Pat. Nos. 4,683,195 and 4,683,202), such as PCR or q-PCR. This method can include the steps of collecting a sample of cells from a subject (such as a brush cytology sample), extracting nucleic acids (e.g., cDNA generated from mRNA, mRNA or both) from the cells of the sample, contacting the nucleic acid sample with one or more primers which specifically hybridize to a gene under conditions such that hybridization and amplification of the gene (if present) occurs, and detecting the expression level of an amplification product, and comparing the expression level to a standard.

In other embodiments, intensity assessment in electrophoretic mobility can be used to identify expression level of genes or genes encoding a protein of the invention. For example, amplification of the cDNA generated from the mRNA can be performed and the reaction product can be measured and quantified by electrophoresis.

Figure 7A:
FIG. 7A shows a bar graph comparing expression of the B2M gene in brush cytology samples from 13 animals. Each bar represents the relative mRNA level of one of three samples taken on consecutive weeks from oral squamous cell carcinoma tumor in five hamsters and normal mucosa of eight control hamsters. Shown is the mean of three PCR runs of a single sample. For each animal the overall intraclass correlation (ICC) among each set of three measurements was calculated.
Figure 7B:
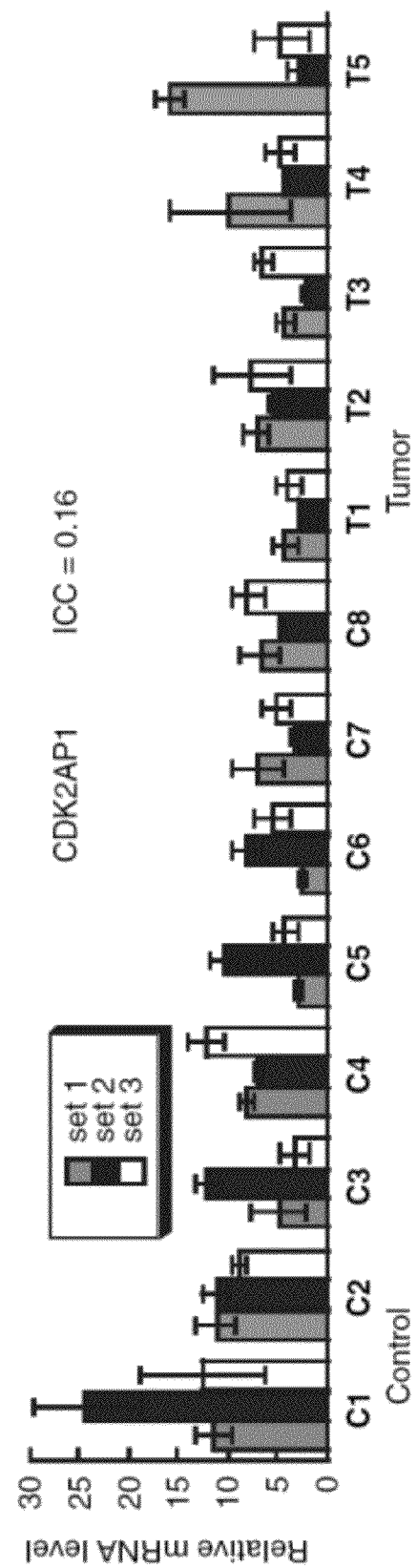
FIG. 7B shows a bar graph comparing expression of the CDK2AP1 gene in brush cytology samples from 13 animals.
Figure 7C:
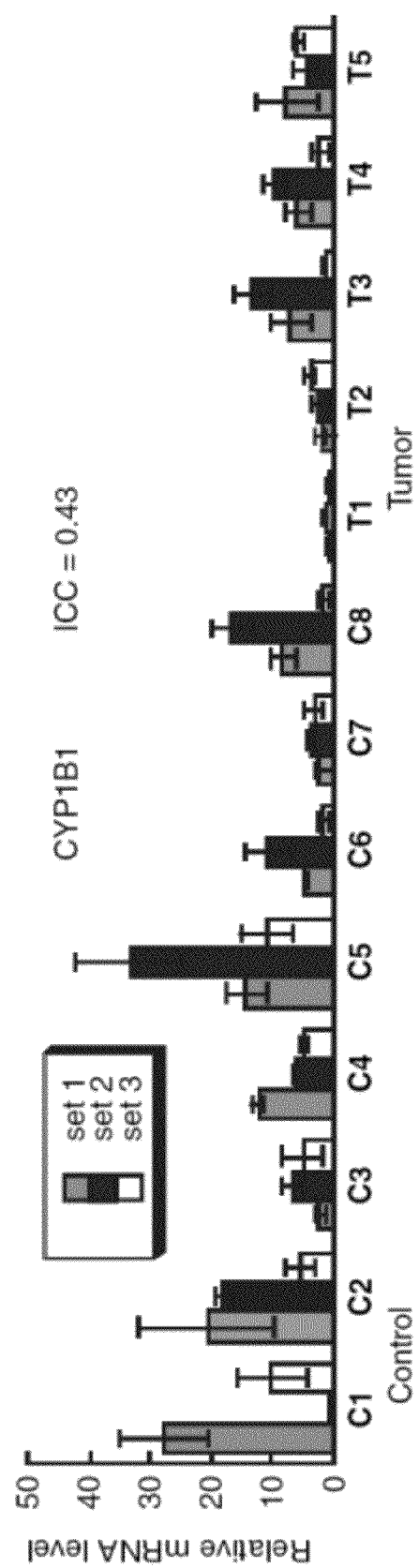
FIG. 7C shows a bar graph comparing expression of the CYP1B1 gene in brush cytology samples from 13 animals.
Figure 7D:
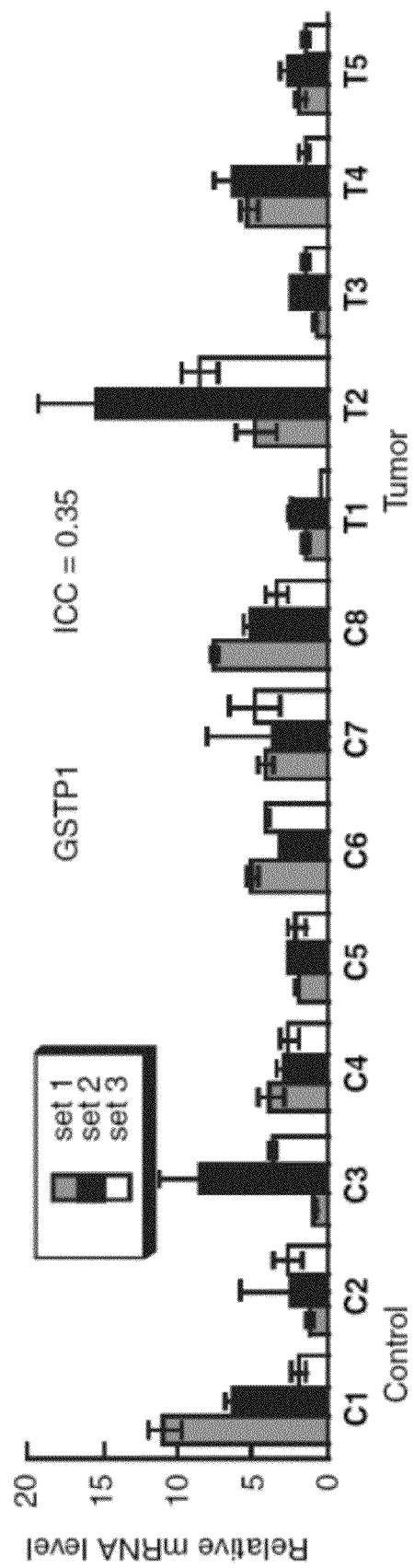
FIG. 7D shows a bar graph comparing expression of the GSTP1 gene in brush cytology samples from 13 animals.
Figure 7E:
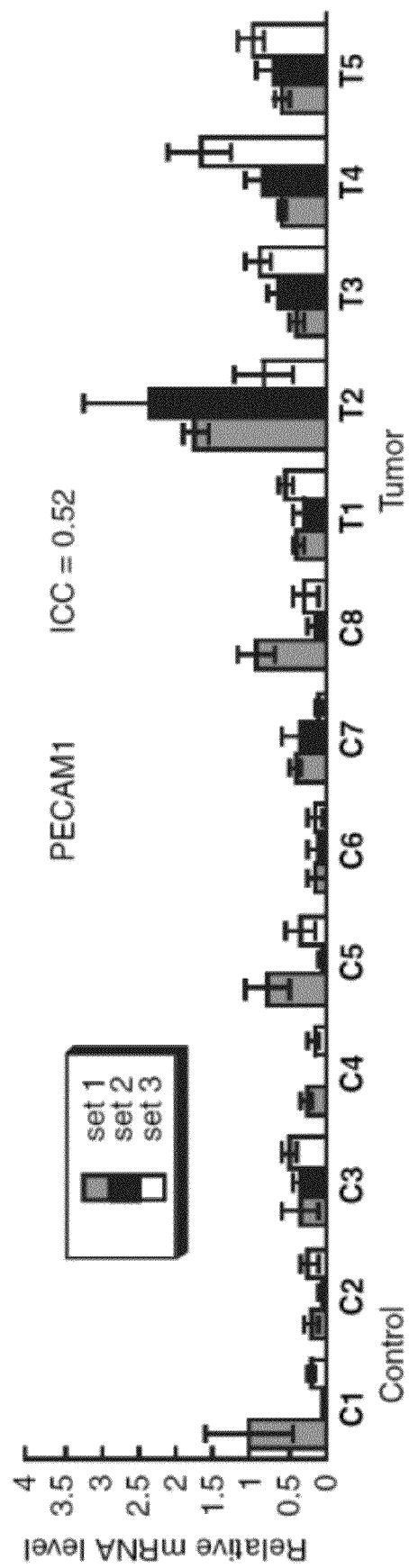
FIG. 7E shows a bar graph comparing expression of the PECAM1 gene in brush cytology samples from 13 animals.
Figure 7F:
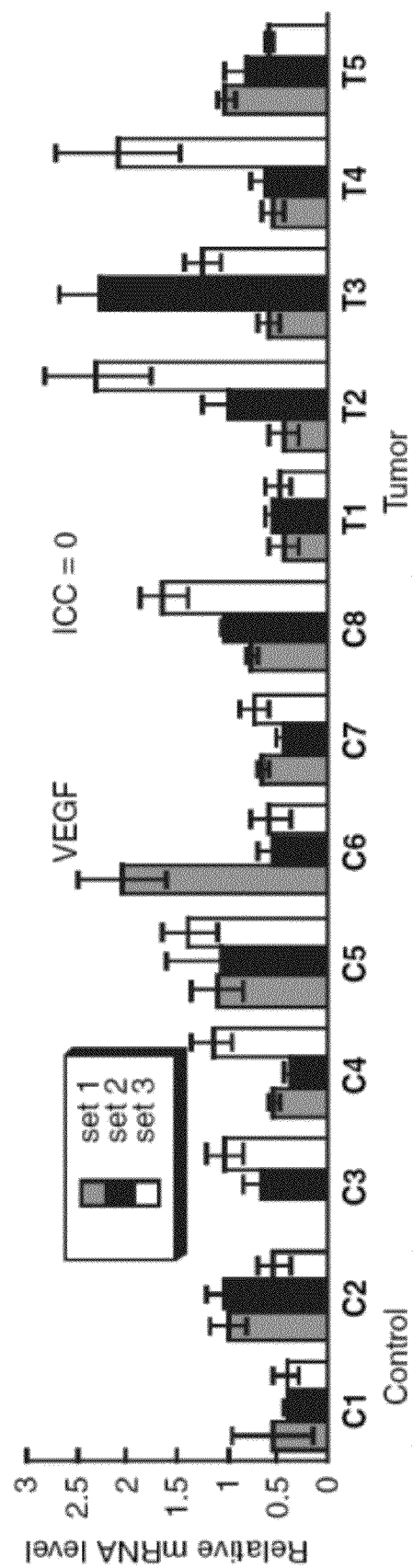
FIG. 7F shows a bar graph comparing expression of the VEGF gene in brush cytology samples from 13 animals.
Figure 8A:
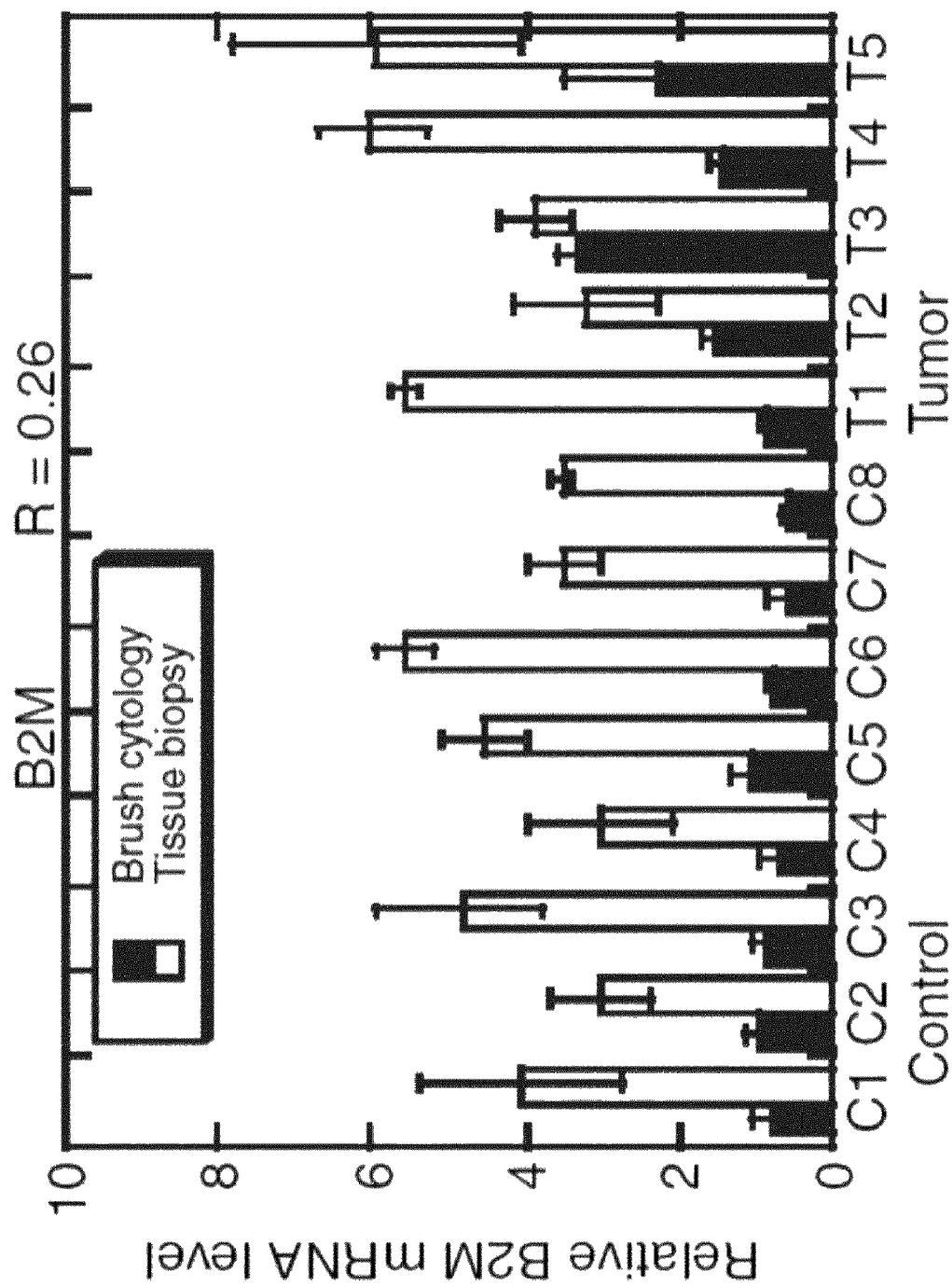
FIG. 8A shows a bar graph comparing measured B2M mRNA levels in brush cytology RNA samples vs. surgically excised (biopsy) tissue from 13 animals. The mean mRNA levels for each tested gene were calculated for brush cytology samples (black bars) vs. surgically removed tissue (white bars)±SEM. The values for the brush cytology cell mRNA were averaged over three separate brush cytology samples. The correlation coefficient (R) comparing the derived values from the two cell sources for each hamster was derived.
Figure 8B:
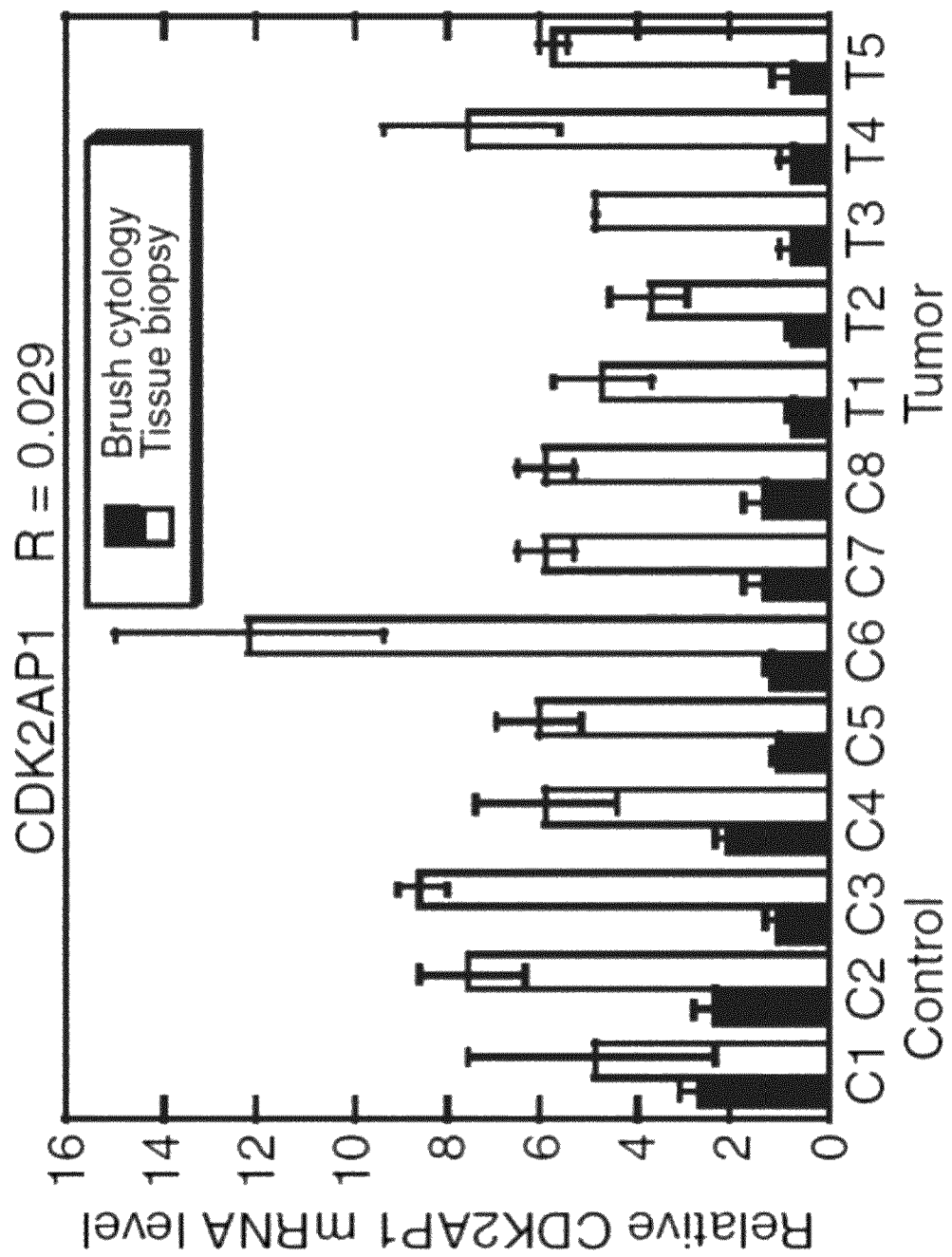
FIG. 8B shows a bar graph comparing measured CDK2AP1 mRNA levels in brush cytology RNA samples vs. surgically excised (biopsy) tissue from 13 animals.
Figure 8C:
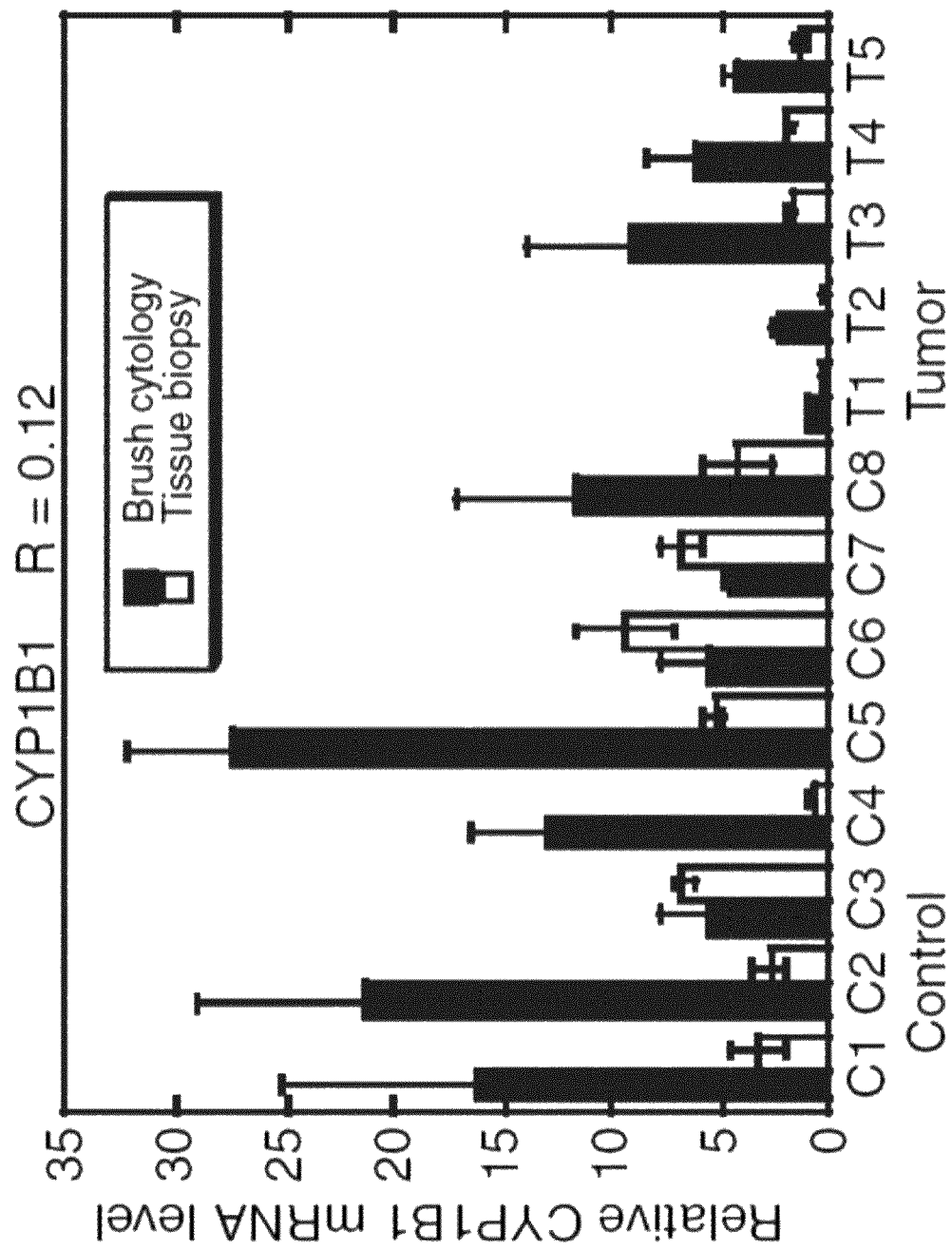
FIG. 8C shows a bar graph comparing measured CYP1B1 mRNA levels in brush cytology RNA samples vs. surgically excised (biopsy) tissue from 13 animals.
Figure 8D:
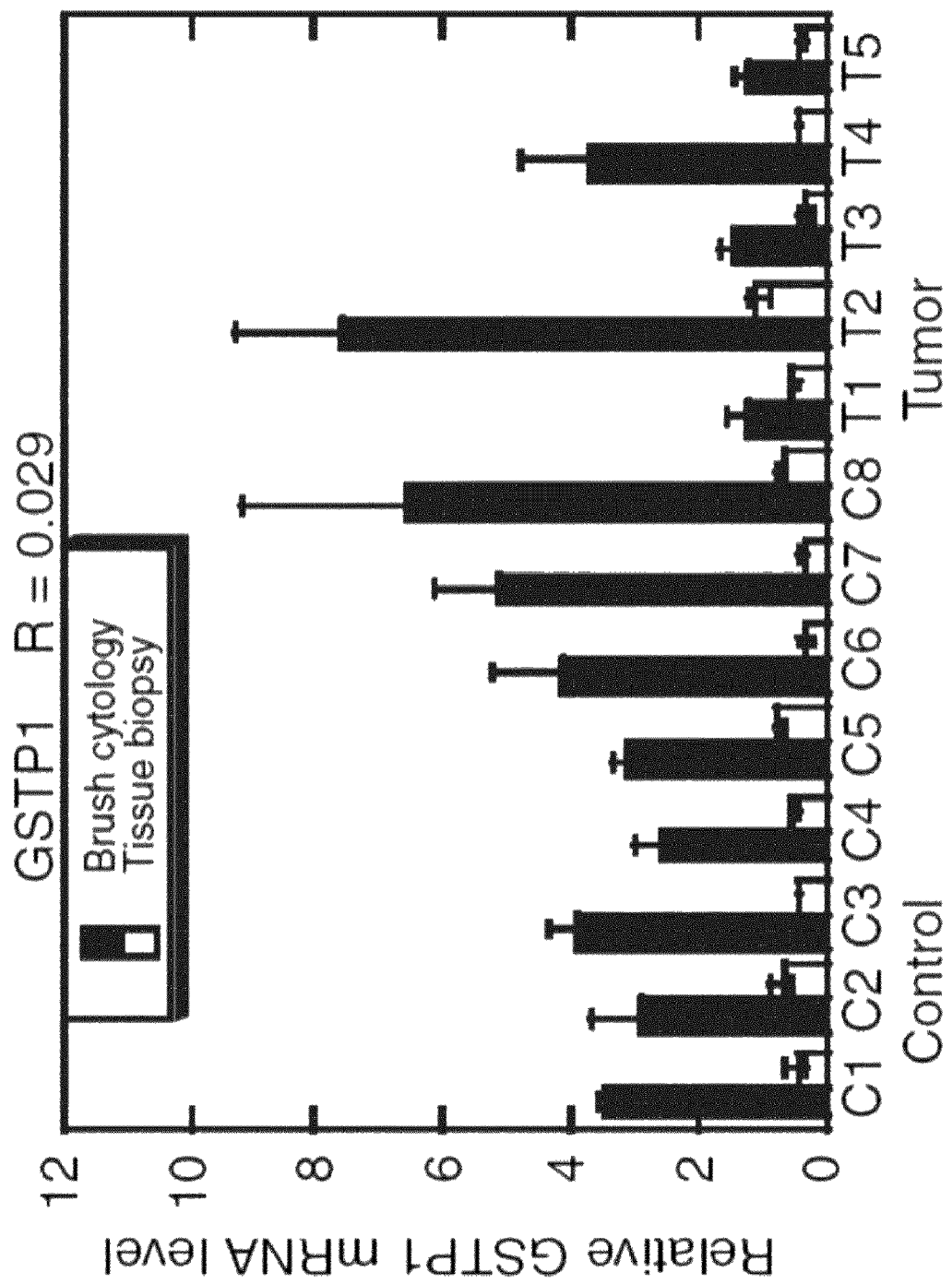
FIG. 8D shows a bar graph comparing measured GSTP1 mRNA levels in brush cytology RNA samples vs. surgically excised (biopsy) tissue from 13 animals.
Figure 8E:
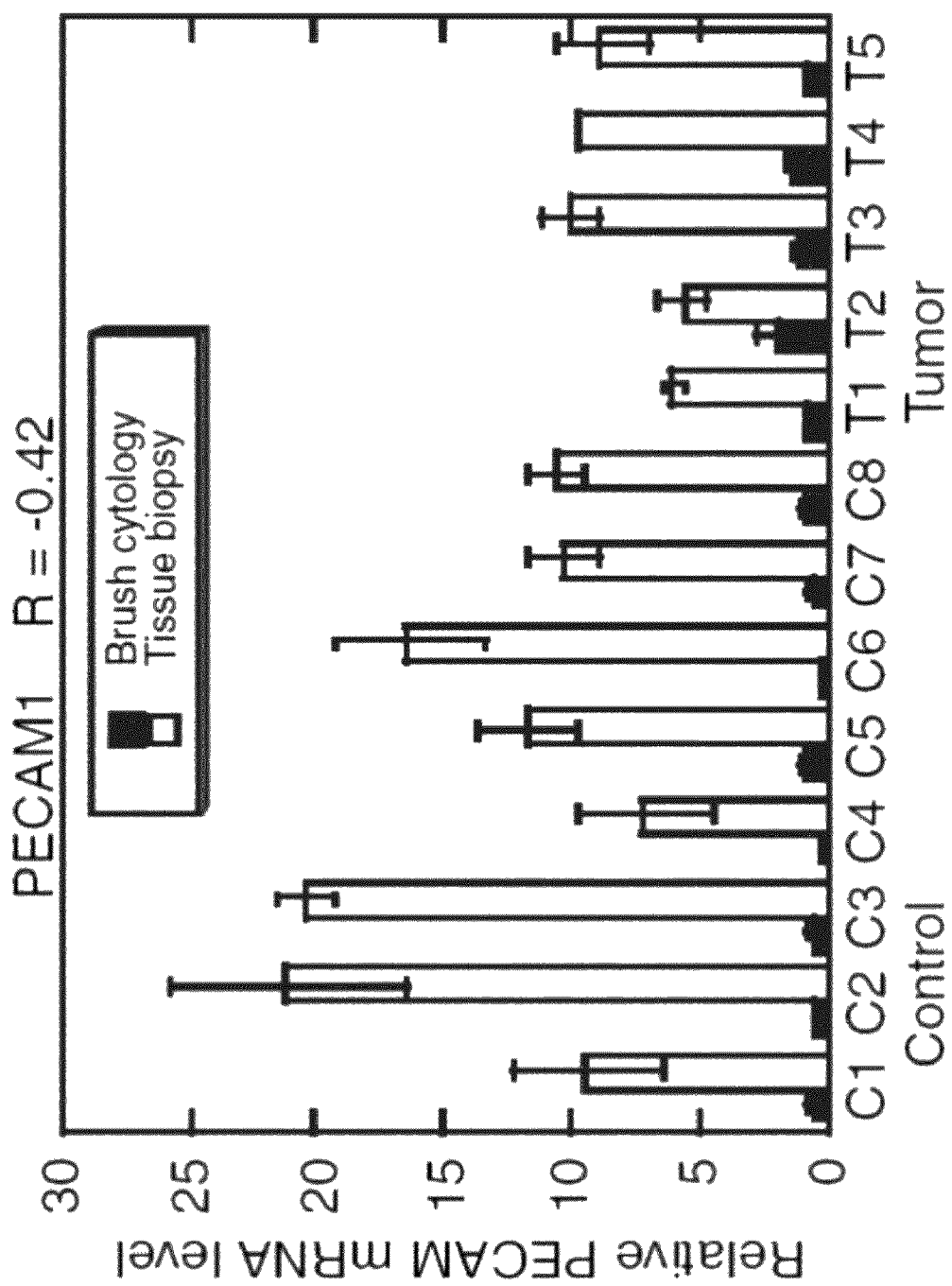
FIG. 8E shows a bar graph comparing measured PECAM1 mRNA levels in brush cytology RNA samples vs. surgically excised (biopsy) tissue from 13 animals.
Figure 8F:
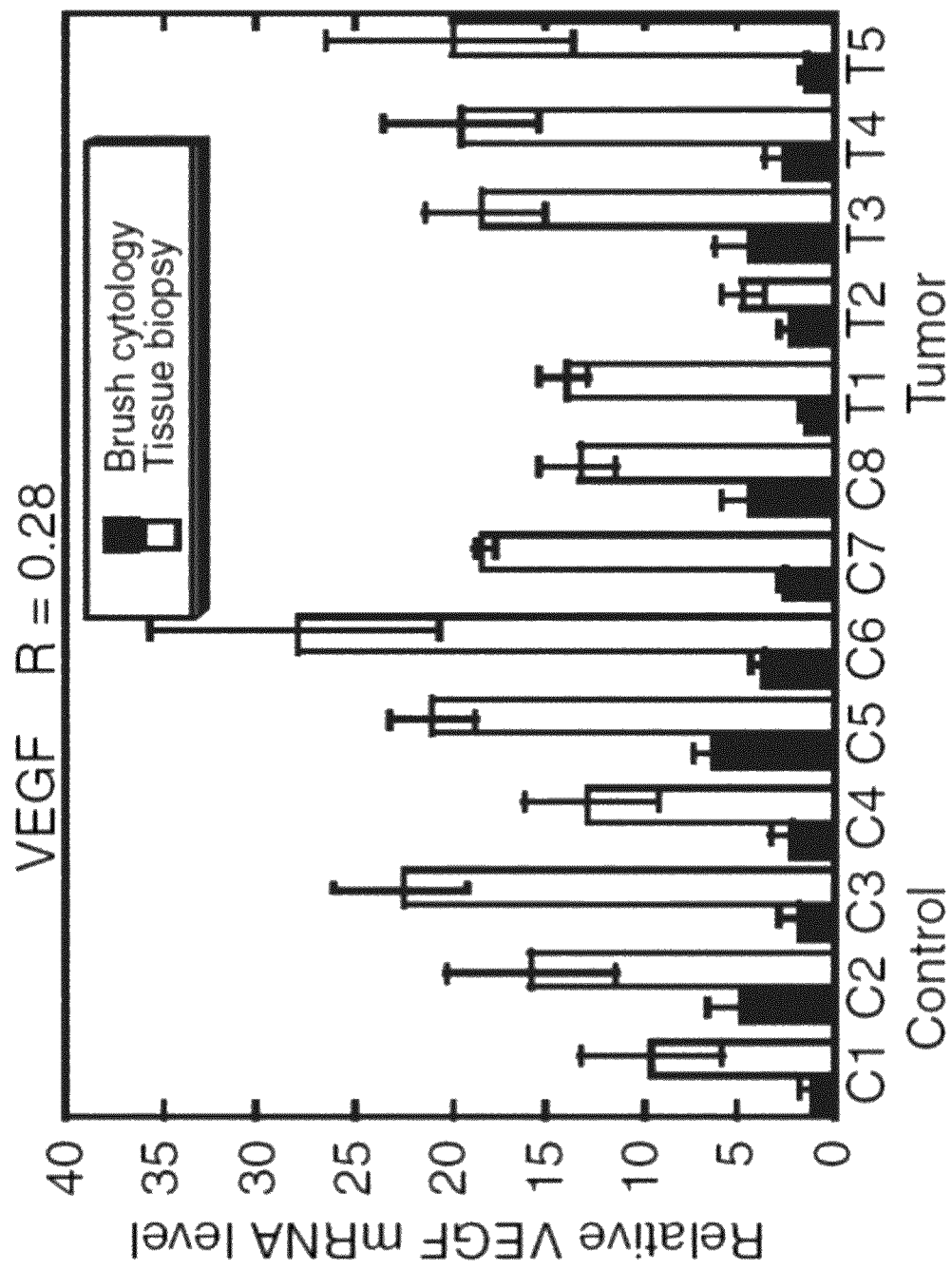
FIG. 8F shows a bar graph comparing measured VEGF mRNA levels in brush cytology RNA samples vs. surgically excised (biopsy) tissue from 13 animals.

In one aspect of the invention, the results from assaying expression levels of tumor-associated genes, such as B2M and CYP1B1, can influence a treatment prescribed by a health care practitioner or other person of known skill in the art. Based on the analyzed expression levels of the tumor-associated genes, such as B2M and CYP1B1, additional assessments can be made to determine a treatment. The type of treatment options can be determined by those skilled in cancers. In some embodiments, repeated sampling can be done to monitor the progression of the squamous cell neoplasia over time when aberrant expression of tumor-associated genes is detected in initial assays. Some treatments can also include administering bioactive agents that act as inhibitors of cytochrome p450 family members. These inhibitors can potentially inhibit the overexpression of cytochrome p450 1B1 that is demonstrated in FIGS. 7C and 8C. Inhibitors can also be administered to treat a squamous cell neoplasia by inhibiting cytochrome p450.

3. Monitoring of the Progression of Neoplasia

Monitoring the cancer, e.g., squamous cell neoplasia, in a subject over time by assessing the expression of genes (e.g., B2M and CYP1B1) can monitor the progression of the squamous cell neoplasia. For example, the progression of squamous cell neoplasia over time can comprise an increase or decrease of gene expression levels or protein levels indicative of progression or inhibition of the neoplasia. Alternatively, the effectiveness of a treatment or the influence of agents (e.g., drugs) on the squamous cell neoplasia, can increase or decrease gene expression levels or protein levels. In such clinical trials, the expression levels of a gene or genes can be used as a "read out" of the progression or inhibition of the neoplasia.

For example, and not by way of limitation, genes, including genes of the invention and proteins encoded by the genes, that are altered by treatment with an agent (e.g., compound, drug or small molecule) can be identified. Thus, to study the effect of agents on gene-associated disorders (e.g., squamous cell carcinoma), for example, in a clinical trial, samples can be obtained and nucleic acids or proteins can be extracted and assayed for expression levels. The expression levels can be assayed by q-PCR, as described herein, or alternatively by measuring the amount of nucleic acid or protein produced, by one of the methods as described herein. In this way, the expression levels can be indicative of the physiological response of the neoplasia to the agent. Accordingly, the expression levels can be assayed before, and at various points during treatment with the agent.

In a preferred embodiment, the present invention provides a method for monitoring squamous cell neoplasia in a human subject over time including the steps of (i) obtaining a brush cytology sample from a subject at a first time; (ii) extracting nucleic acids from cells in the sample; (iii) assaying said nucleic acids for the expression level of genes coding for the production of beta-2 microgobulin (B2M) and cytochrome p450 1B1 (CYP1B1); and (iv) repeating the steps of obtaining a sample, extracting nucleic acids and assaying for expression levels of B2M and CYP1B1 at a later time, wherein increased expression of the B2M gene at a later time or decreased expression of the CYP1B1 gene at a later time is indicative of progression of neoplasia.

In another embodiment, squamous cell neoplasia in a human subject can be monitored over time in response to a treatment. A sample can be obtained, nucleic acids extracted from the sample, expression level of genes encoding for beta-2 microgobulin (B2M) and cytochrome p450 1B1 (CYP1B1) can be assayed, a treatment can be administered, wherein the treatment is a bioactive agent that inhibits cytochrome p450 proteins, sampling from the subject can be repeated over time and the expression level of B2M and CYP1B1 at a later time is indicative of the response to the treatment.

4. Kits for Detecting Cancer

The present invention also provides a kit that can be used in the above methods. A kit for assessing cancer in a sample of the present invention includes a means of detecting the expression levels of beta-2 microglobulin (B2M) gene or a cytochrome p450 1B1 (CYP1B1) genes in a sample. The present kit for cancer can include reagents used to make a diagnosis of cancer. Also, the present kit for cancer can comprise components used in publicly known kits, except that a means of detecting the expression level of genes associated with cancer (e.g., B2M and CYP1B1). Further, with the use of the kit for cancer, it can be possible to diagnose a subject as having cancer. Examples of cancer include, but are not limited to, squamous cell carcinoma. The kit can also be used to monitor progression of squamous cell neoplasias, as described above.

Herein, examples of detecting the presence of cancer by assaying expression levels cancer associated genes, can comprise:

(1) a pair of primers which specifically hybridize to at least one non-degraded nucleic acid sequences coding for production of beta-2 microglobulin (B2M) gene or a cytochrome p450 1B1 (CYP1B1) gene; and (2) reagents for real-time polymerase chain reaction (q-PCR).

In additional embodiments the kit can comprise additional tools, reagents or instruction manuals. For example, the kit can comprise reagents for cDNA synthesis, a brush for obtaining a brush oral cytology sample from a subject. Also, the kit can comprise a nucleic acid extraction reagent to isolate nucleic acids from a sample.

In one embodiment, the kit can be a diagnostic kit for use in testing a sample. The kit can comprise one or more suitable pairs of primers for simultaneous or individual reverse transcription of different genes associated with cancer, such as B2M and CYP1B1, and optionally an appropriate calibrator mRNA in a single cDNA-synthesis reaction. standards or controls for q-PCR and/or standards or controls for B2M and CYP1B1 expression levels. The kit of the invention can be particularly useful for carrying out a variety of highly sensitive real-time PCRs (q-PCRs), thus allowing the quantification of expression levels of the tumor-associated genes, such as B2M and CYP1B1. For example, such a kit can include reagents for detecting expression levels of cancer associated genes, such as B2M and CYP1B1 (for example, primers and q-PCR reagents).

Another embodiment of the present invention, the kit can contain instruction and reagents to simultaneously prime the reverse transcription of mRNA from more than one tumor associated genes in a single cDNA-synthesis reaction. Simultaneous quantification of genes by highly sensitive (reverse transcriptase PCR, RT-PCR) of the invention can reliably convert mRNA to cDNA by reverse transcription with reproducible efficiency.

In yet another embodiment, the kit can be used as a screening kit for presence of cancer in a sample or a series of samples. The kit can further be used as a method for monitoring the progression of a squamous cell neoplasia.

In one aspect of the invention, the kit can be used to determine expression levels of tumor-associated genes, such as B2M and CYP1B1, which can influence a treatment prescribed by a health care practitioner or other person skilled in the art. The type of treatment can be determined by those skilled in cancers and based on the results from the kit which analyzes expression levels of the tumor-associated genes, such as B2M and CYP1B1. In another embodiment, additional kits can be used over time to monitor the progression of the squamous cell neoplasia when over expression of B2M and CYP1B1 is detected. In another embodiment, multiple kits can be used over time to monitor the progression or inhibition of squamous cell neoplasia in response to a treatment with a bioactive agent by monitoring expression levels of B2M and CYP1B1.

IV. Isolated Nucleic Acid and Proteins and Detection Methods

One aspect of the invention pertains to extracting nucleic acid molecules that either themselves are the nucleic acid sequences of interest (e.g., mRNA) of the invention, or which encode the polypeptide of the invention, or fragments thereof. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded.

The term "extracted nucleic acid molecule" includes nucleic acid molecules which are separated from other molecules, such as other nucleic acid molecules or cellular debris which can be present within or associated with cells. For example, with regards to RNA, the term "isolated" includes RNA molecules which are separated from the other nucleic acids which are normally associated with RNA, such as DNA. Moreover, an "extracted" nucleic acid molecule, such as a cDNA molecule, can be substantially free of other cellular material, or culture medium when produced by recombinant techniques, or substantially free of chemical precursors or other chemicals when chemically synthesized. Nucleic acid molecules can be isolated from a cellular sample through means known by those skilled in the art, such as through cell lysis and precipitation and/or use of commercial reagents specialized in nucleic acid extraction.

A nucleic acid molecule of the present invention, e.g., a nucleic acid molecule having the nucleotide sequence of the gene or a portion thereof, can be isolated using standard molecular biology techniques and the sequence information provided herein. Using all or a portion of the nucleic acid sequence of the gene as a hybridization probe, a gene of the invention or a nucleic acid molecule encoding a polypeptide of the invention can be isolated using standard hybridization and cloning techniques (e.g., as described in Sambrook, J., Fritsh, E. F., and Maniatis, T. *Molecular Cloning: A Laboratory Manual*. 2nd, ed, Cold Spring Harbor Laboratory, Cold Spring Harbor Laboratory Press, Cold Spring Harbor, N.Y., 1989).

A nucleic acid of the invention can be amplified and quantified using mRNA or cDNA generated from mRNA as a template and appropriate oligonucleotide primers according to standard PCR amplification techniques and quantitative methods, such as q-PCR. The nucleic acids of the invention, moreover, can comprise non-degraded nucleic acid sequences coding for production of beta-2 microgobulin (B2M) and cytochrome p450 1B1 (CYP1B1). In a more refined approach, cDNA copies of these mRNAs can be made using reverse transcriptase by methods known to those skilled in the art. A probe/primer can be generated to a specific portion of the genes to assay non-degraded mRNA, such as at least 500 basepairs and preferably at least 1000 basepairs from the encoded 3' ends of the transcripts. The primers can be generated or purchased, as described above, such that they hybridize to at least about 10 to 12, preferably at least 15, found near at least 500 basepairs and preferably at least 1000 basepairs from the encoded 3' ends of the transcripts of the invention.

In another embodiment, extracted nucleic acids of the invention can be at least 50, 100, 150, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000 or more nucleotides in length and hybridizes to a nucleic acid molecule corresponding to a nucleotide sequence of a gene.

In one embodiment, proteins can be extracted from cells or tissue sources by an appropriate purification scheme using standard protein purification techniques. An "extracted" or "purified" protein or portion thereof is substantially free of cellular material or other contaminating proteins from the cell or tissue source from which the protein is derived, or substantially free from chemical precursors or other chemicals when chemically extracted. The language "substantially free of cellular material" includes preparations of protein in which the protein is separated from cellular components of the cells from which it is isolated or recombinantly produced. In one embodiment, the language "substantially free of cellular material" can include preparations of protein having less than about 30% (by dry weight) of other proteins (also referred to herein as a "contaminating protein"), more preferably less than about 20% of other proteins, still more preferably less than about 10% of other proteins, and most preferably less than about 5% other proteins. When the protein or portion thereof is chemically extracted, it can also be substantially free of chemical used for extraction, i.e., chemical represent less than about 20%, more preferably less than about 10%, and most preferably less than about 5% of the volume of the protein preparation.

As used herein, a "portion" of the protein includes a fragment of the protein comprising amino acid sequences sufficiently homologous to or derived from the amino acid sequence of the protein, which include fewer amino acids than the full length proteins. Typically, portions of the protein can comprise a domain or motif with at least one activity of the protein. A portion of the protein can be a polypeptide which is, for example, 10, 25, 50, 100, 200 or more amino acids in length. Portions of the protein can be used as targets for developing agents which modulate expression levels of the protein.

The proteins or nucleic acid sequences of the invention can be detected by any method known to those of skill in the art. A wide variety of conventional techniques are available, including mass spectrometry, chromatographic separations, 2-D gel separations, binding assays (e.g., immunoassays), competitive inhibition assays, and so on. Any effective method in the art for measuring the present/absence, level or activity of a protein or nucleic acid sequence is included in the invention. It is within the ability of one of ordinary skill in the art to determine which method would be most appropriate for measuring a specific protein or nucleic acid sequence. Thus, for example, a ELISA assay may be best suited for use in a physicians office while a measurement requiring more sophisticated instrumentation may be best suited for use in a clinical laboratory. Regardless of the method selected, it is important that the measurements be reproducible.

Quantification can be based on derivatization in combination with isotopic labeling, referred to as isotope coded affinity tags ("ICAT"). In this and other related methods, a specific amino acid in two samples is differentially and isotopically labeled and subsequently separated from peptide background by solid phase capture, wash and release. The intensities of the molecules from the two sources with different isotopic labels can then be accurately quantified with respect to one another. In addition, one- and two-dimensional gels have been used to separate proteins and quantify gels spots by silver staining, fluorescence or radioactive labeling. These differently stained spots have been detected using mass spectrometry, and identified by tandem mass spectrometry techniques.

In other preferred embodiments, the level of the proteins or nucleic acid sequences can be determined using a standard immunoassay, such as sandwiched ELISA using matched antibody pairs and chemiluminescent detection. Commercially available or custom monoclonal or polyclonal antibodies are typically used. However, the assay can be adapted for use with other reagents that specifically bind to the molecule. Standard protocols and data analysis are used to determine the marker concentrations from the assay data.

One embodiment for detecting RNA or DNA corresponding to a gene or protein of the invention can be with the use of a labeled nucleic acid probe capable of hybridizing to a mRNA or cDNA of the invention. Suitable probes for use in the diagnostic assays of the invention are described herein. A preferred agent for detecting protein is an antibody capable of binding to protein, preferably an antibody with a detectable label. Antibodies can be polyclonal, or more preferably, monoclonal. An intact antibody, or a fragment thereof (e.g., Fab or $F(ab')_2$) can be used.

The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling can include detection of a primary antibody using a fluorescently labeled secondary antibody and end-labeling of a DNA probe with biotin such that it can be detected with fluorescently labeled streptavidin. The term "sample" is intended to include tissues, cells and biological samples isolated from a subject (e.g., brush cytology sample), as well as tissues, cells and fluids present within a subject. That is, the detection method of the invention can be used to detect mRNA, protein, or cDNA in a sample in vitro as well as mRNA or protein in vivo. For example, in vitro techniques for detection of mRNA can include PCR, q-PCR, northern hybridizations and in situ hybridizations. In vitro techniques for detection of protein can include enzyme linked immunosorbent assays (ELISAs), western blots, immunoprecipitations and immunofluorescence. In vitro techniques for detection of cDNA can include Southern hybridizations, PCR, q-PCR (e.g., as described in L. Cseke, et al., Handbook of Molecular and Cellular Methods in Biology and Medicine, $2^{nd}$ Ed., CRC Press, 2004). Furthermore, in vivo techniques for detection of protein can include introducing into a subject a labeled antibody. For example, the antibody can be labeled with a radioactive label whose presence and location in a subject can be detected by standard imaging techniques.

Measurement of the relative amount of an RNA or protein molecule of the invention can be by any method known in the art (see, e.g., Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989; and Current Protocols in Molecular Biology, eds. Ausubel et al. John Wiley & Sons: 1992). Typical methodologies for RNA detection include RNA extraction from a cell or tissue sample, followed by hybridization of a labeled probe (e.g., a complementary polynucleotide) specific for the target RNA to the extracted RNA, and detection of the probe (e.g., Northern blotting). Typical methodologies for protein detection include protein extraction from a cell or tissue sample, followed by hybridization of a labeled probe (e.g., an antibody) specific for the target protein to the protein sample, and detection of the probe. The label group can be a radioisotope, a fluorescent compound, an enzyme, or an enzyme co-factor. Detection of specific protein and polynucleotides may also be assessed by gel electrophoresis, column chromatography, direct sequencing, or quantitative PCR (in the case of polynucleotides) among many other techniques well known to those skilled in the art.

Detection of the presence or number of copies of all or a part of a gene of the invention may be performed using any method known in the art. Typically, it is convenient to assess the presence and/or quantity of a DNA or cDNA by Southern analysis, in which total DNA from a cell or tissue sample is extracted, is hybridized with a labeled probe (e.g., a complementary DNA molecule), and the probe is detected. The label group can be a radioisotope, a fluorescent compound, an enzyme, or an enzyme co-factor. Other useful methods of DNA detection and/or quantification include direct sequencing, gel electrophoresis, column chromatography, and quantitative PCR, as is known by one skilled in the art.

The proteins or nucleic acid sequences of the invention can be detected by any method known to those of skill in the art. Primers based on the nucleotide sequence of the genes of the invention can be used to detect transcripts corresponding to the gene(s) of the invention. In some embodiments, a primer pair can be designed by utilizing primer design software, such as GenScript, Primer3, PRIDE and Primer Express. Commercial primers are also available for purchase corresponding to multiple locations throughout the gene. In an exemplary embodiment, the primers can be complementary to an mRNA sequence of at least 15 bases found at least 500 basepairs and preferably at least 1000 basepairs from the encoded 3' ends of the transcripts, corresponding to the transcriptional start site. By specifying at least 500 basepairs and preferably at least 1000 basepairs from the encoded 3' ends of the transcripts for amplification, the q-PCR can be biased toward detecting the expression levels of non-degraded mRNA without interference of degraded mRNA that can be extracted from dead cells or cells undergoing apoptosis.

EXAMPLES

This invention is further illustrated by the following examples which should not be construed as limiting. The following experiments were performed to demonstrate various aspects of the invention.

Example 1

Materials and Methods

Oral Carcinogenesis

Dibenzo[a,I]pyrene was applied orally at a level of 0.025 nm three times a week for 33 weeks to produce floor of the mouth and lateral border of tongue tumors in Golden Syrian Hamster (*Mesocricetus auratus*). Five of 12 animals developed oral squamous cell carcinoma (OSCC) detectable by gross inspection. These were later verified histologically. The average cross-sectional area of the lesions in these five was 3.2 mm². The first samples were taken from these five hamsters 1 month after the end of the carcinogen exposure (week 37). This was to insure that the observed gene expression changes were due to longterm changes in the tissue and not directly due to the presence of 0.0025 nM dibenz[a,I]pyrene. Eight hamsters treated identically but never exposed to dibenzo[a,I]pyrene were used as the source of control tissue. All procedures were carried out within the guidelines of the Animal Research Committee at the University of Illinois at Chicago.

Cell and Tissue Acquisition

For brush cytology, a Cytosoft' brush (Cytology Brush, Medical Packaging Corp., Camarillo, Calif., USA) was used to harvest oral keratinocytes from the mucosa, between 2:00 and 3:30 PM, on three consecutive weeks (weeks 37, 38, and 39). Twenty back and forth brushing motions were used. No trauma to the mucosa was noted. Brush oral cytology was applied to oral carcinoma and non-oral carcinoma sites. On the $40^{th}$ week, normal and tumor-bearing mucosa was surgically removed following asphyxiation with bottled carbon dioxide.

Histopathology to Identify Oral Cancer

Tissues were processed, embedded, and sectioned at 5 um. Sections were stained using hematoxylin and eosin using an automated autostainer (Leica Microsystems, Bannokbum, Ill., USA) and evaluated using standard criteria.

Immunohistochemistry

Cells were fixed in 2.5% formalin overnight then subjected to immunofluorescent staining using pancytokeratin-specific antibodies, clones: AE-1 and AE-3 (ab961) (AbCam, Cambridge, UK) as directed. The Ventana HX system (Ventana, Yokohama, Japan) was used to perform the immunofluorescent staining according to the manufacturer's protocol with standard enzymatic antigen retrieval. Tissue was treated identically except it was fixed in 10% formalin overnight and imbedded in paraffin prior to sectioning.

RNA Extraction

Following brush cytology cell collection the brush was immersed in Trizol (Invitrogen, Carlsbad, Calif., USA), vortexed and then frozen at) 70° C. On thaw, the sample was vortexed, and then subjected to standard RNA isolation, followed by DNAse 1 treatment with the Aurum Total RNA Mini-kit as described by the manufacturer (Bio-Rad, Hercules, Calif., USA). cDNA synthesis was performed with ⅓ of the total sample of RNA, using random hexamers and Superscript III RT enzyme (Invitrogen). A similar process was used for the isolation of RNA from tissue, except mechanical homogenization was required in Trizol (Invitrogen).

Quantitative Real-Time q-PCR

Quantitative real-time q-PCR was carried out using the iCycler iQ (Bio-Rad) and SYBR Green fluorescence to detect double-stranded DNA. Values were normalized to the best controls, succinate dehydrogenase complex A (SDHA) and glyceraldehyde-3-phosphate dehydrogenase (GAPD) for brush cytology samples and cyclophilin A (PPIA) and beta-actin (ACTB), for tissue and brush cytology samples together. The quality of the RNA was judged to be satisfactory based on the fact that q-PCR with PPIA primer sets with different product sizes (120, 150, and 182 nucleotides) all gave similar results. Negative controls were without reverse transcriptase for cDNA synthesis. Amplicon sizes for primer pair products were validated using standard q-PCR with agarose gel ethidium bromide visualization. The results are reported as mean values from 3 to 6 separate samples. All PCR runs included a reference cDNA to allow the comparison of expression levels of samples tested at different times. Primer sets used included: forward primer hamster B2M (3' AGTTTGTACCCACTGCGACTGA 5') (SEQ ID NO.: 3); reverse primer hamster B2M (3' TGCTGCTGTGTGCATAGACTGA 5') (SEQ ID NO.: 4); forward primer human B2M (3' TGTGCTCGCGCTACTCTCTCTTT 5') (SEQ ID NO.: 5); reverse primer human B2M (3' ATGTCGGATGGATGAAACCCAGAC 5') (SEQ ID NO.: 6); forward primer hamster CYP1B1 (3' GAATCCATGCGCTTCTCCAGCTTT 5') (SEQ ID NO.: 7); reverse primer hamster CYP1B1 (3' TCCAGGAATCGGGCTGGATCAAAT 5') (SEQ ID NO.: 8); forward primer human CYP1B1 (3' GCCTCATTATGTCAACCAGGTCCA 5') (SEQ ID NO.: 9), and reverse primer human CYP1B1 (3' AAGCCAGGTAAACTCCAAGCACCT 5') (SEQ ID NO.: 10).

Determination of Endogenous Controls for mRNA Levels of Brush Oral Cytology Harvested RNA Direct analysis for RNA concentrations in brush cytology samples was impractical because of the low amounts (estimated at 20-200 ng), so the identification of reference genes to control for the mRNA levels was of great importance, see Table 1 (Sample 1 and 2 from Patient 1 and Sample A, B and C from Patient 2). Potential housekeeping genes for this purpose were identified based on their constant expression in many tissues or on consistent levels in normal and tumor tissue of the gastrointestinal tract based on data contained at the SAGEmap site of the Cancer Genome Anatomy Project.

Of the candidates, cDNA sequences for four (ACTB, GAPD, PPIA, and SDHA) were available in the Syrian Golden Hamster database, and a fifth, GSTP1, was added based on our observation that its expression was similar on average in tumor and normal oral mucosa (see FIGS. 8A-8F). We determined the expression level of these genes in brush cytology samples from eight examples of normal tissue and 10 examples of tumor tissue. We used the NORMFINDER program to identify the optimal control(s). This program determined which gene(s) varied minimally in expression levels when compared to average expression of the other potential reference genes. For tumor and control brush cytology samples (as in FIGS. 7A-7F) the geometric mean of the SDHA and GAPDH levels was identified as an optimal internal standard. Analogously, for tumor and control RNA from cytology and tissue biopsy samples together (as in FIGS. 8A-8F), the geometric mean of ACTB and PPIA levels was an optimal control.

TABLE 1

Proportion of undegraded Human beta actin mRNA in different samples

|  | Sample 1 | Sample 2 | Sample A | Sample B | Sample C |
| --- | --- | --- | --- | --- | --- |
| Product-5' | .0072 | .042 | .016 | 1.8 | 1 |
| Product-3' | .45 | 1.2 | .186 | 1.8 | 3 |
| 5'/3' | .016 | .034 | .086 | 1 | .33 |

Statistical Analysis

The data presented are mean±SD unless otherwise stated. For statistical comparison of RNA levels between the control and tumor groups the Student's t-test was used. Results were considered statistically significant if the two-tailed P-values were <0.05. Analysis of variance (ANOVA) was used for the determination of the intraclass correlation (ICC) for repeated tests on the same hamster (FIGS. 7A-7F).

Example 2

Experimental Results

Reliability of Quantitation of Brush Cytology Sample RNA

Figure 6A:
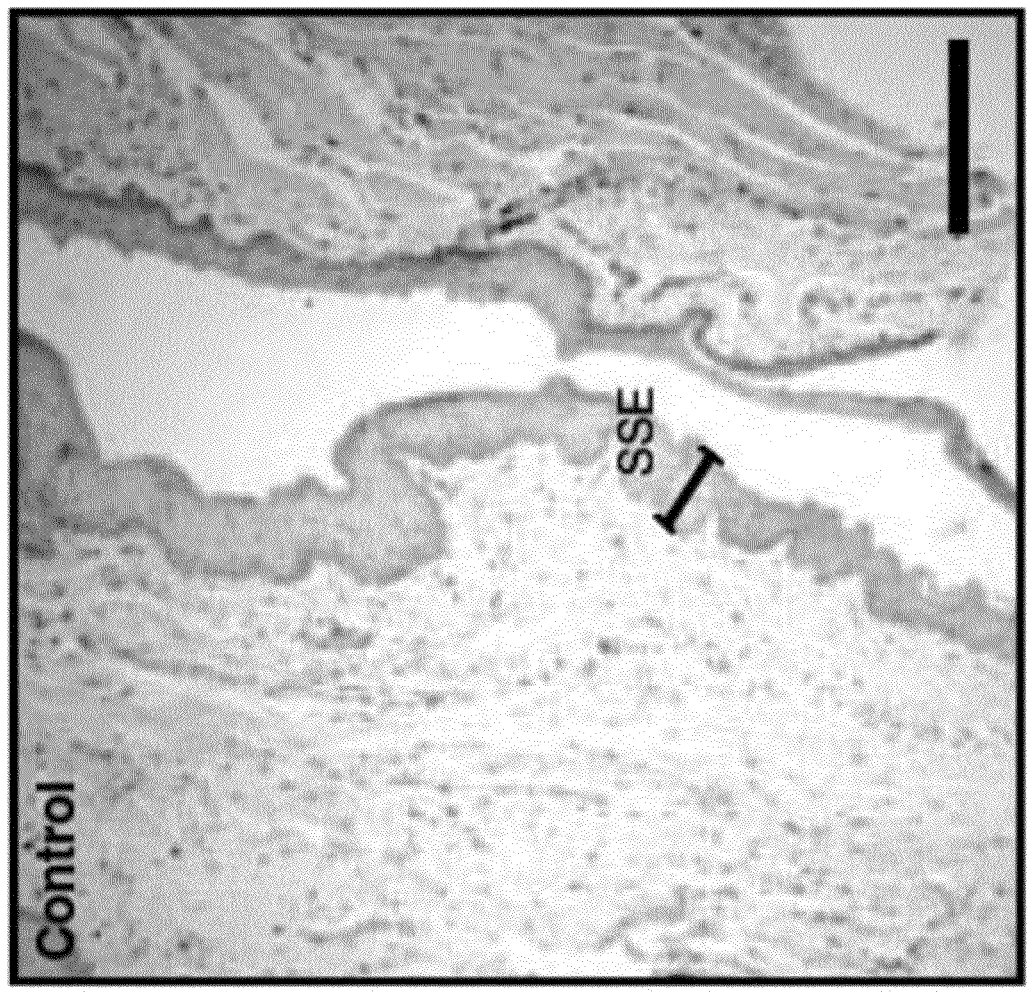
FIG. 6A shows hematoxylin and eosin-stained tissue sections from control unexposed hamster oral tissue (floor of mouth and lateral border of tongue) (bar=200 lm), with one example of stratified squamous epithelium (SSE) labelled.
Figure 6B:
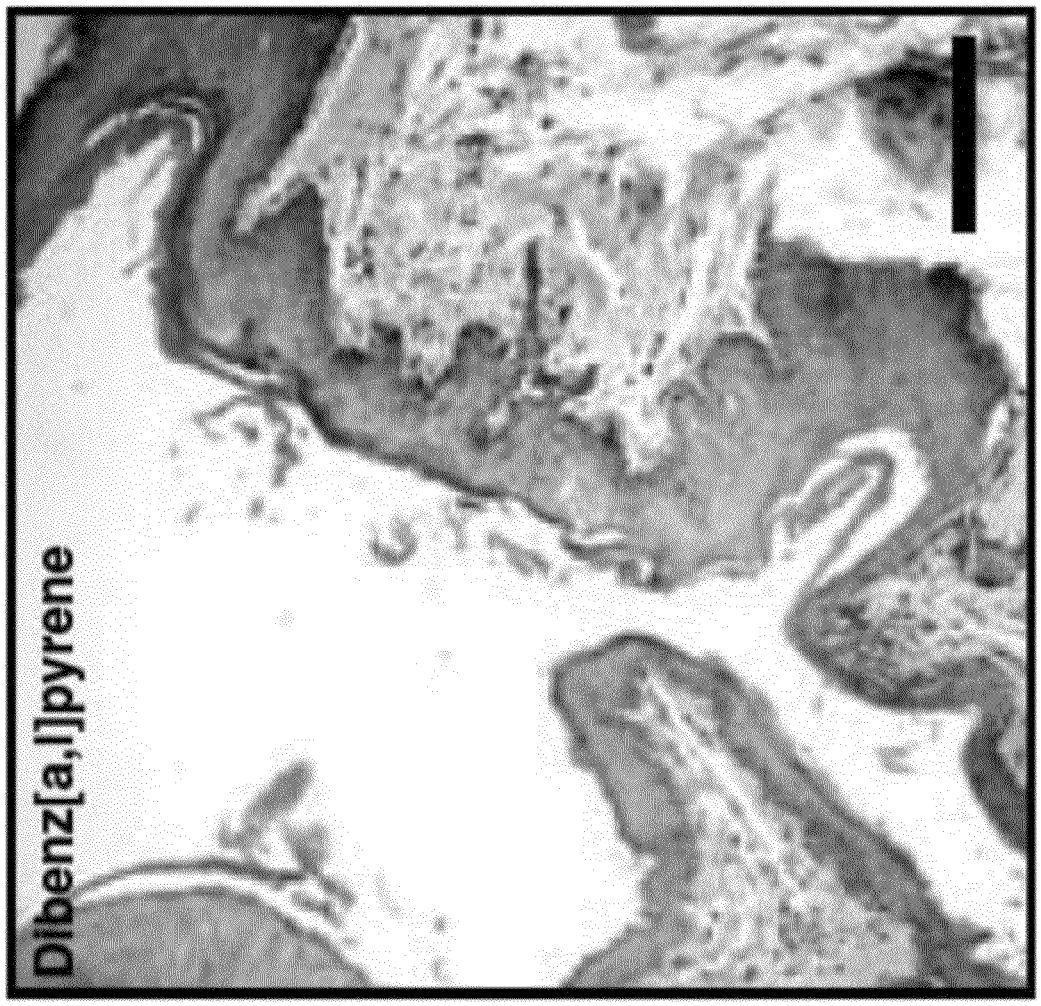
FIG. 6B shows hematoxylin and eosin-stained tissue sections after 33 weeks of exposure to dibenzo[a,l]pyrene that reveal histopathologic changes characteristic of oral squamous cell carcinoma (bar=200 lm)

One month after the end of the dibenzo[a,l]pyrene exposure, brush cytology samples were harvested on three consecutive weeks from diseased and control unexposed hamsters (FIGS. 6A and 6B). RNA was purified and subjected to real-time q-PCR analysis (FIGS. 7A-7F). We used these two sources of cells (tumor epithelium and control mucosa) to increase the probability that specific RNA expression levels would vary among the different animals. The bar graphs in FIGS. 7A-7F show the measured level for each RNA of interest and allows an analysis of the reliability of the methodology described here. In addition to the tumor-associated genes, expression of the endothelial cell marker PECAM1 was also measured. The ICC was calculated as a measure of the degree of similarity between measurements carried out at different times for the same animal. It is compared to the degree of similarity of measurements for the different animals. While there was substantial lack of similarity for the weekly measurements on the same animal for some mRNAs, for three there was a relatively large ICC (FIGS. 7A-7F), verifying that there was substantial reproducibility in the measurement method. Nevertheless, it was clear that multiple samples would be necessary for the greatest accuracy. We also note that for three of six mRNAs (B2M, CYP1B1, and PECAM1), there were significant differences in expression levels in tumor vs. control samples (see Table 2).

TABLE 2

Comparison of mRNA levels in control vs. tumor in samples acquired by different methods

| | Method of cell acquisition | |
|---|---|---|
| Gene | Brush cytology | Tissue biopsy |
| B2M | | |
| Control | 1.08 ± 0.111 | 4.00 ± 0.322 |
| Tumor | 2.59 ± 0.446 | 4.92 ± 0.576 |
| P-value | 0.00271 | 0.158 |
| CDK2AP1 | | |
| Control | 1.55 ± 0.168 | 7.11 ± 0.820 |
| Tumor | 0.709 ± .0847 | 5.31 ± 0.632 |
| P-value | 0.0643 | 0.149 |
| CYP1B1 | | |
| Control | 13.2 ± 2.89 | 4.99 ± 0.96 |
| Tumor | 4.65 ± 1.42 | 1.22 ± 0.35 |
| P-value | 0.0154 | 0.0123 |
| GSTP1 | | |
| Control | 3.99 ± 0.419 | 0.50 ± 0.06 |
| Tumor | 2.98 ± 0.750 | 0.51 ± 0.14 |
| P-value | 0.862 | 0.941 |
| PECAM1 | | |
| Control | 0.447 ± 0.0781 | 13.3 ± 0.1.88 |
| Tumor | 1.10 ± 0.202[a] | 8.01 ± 0.938 |
| P-value | 0.00129 | 0.0572 |
| VEGF | | |
| Control | 3.34 ± 0.478[a] | 15.3 ± 2.84 |
| Tumor | 2.43 ± 0.497 | 17.6 ± 2.12 |
| P-value | 0.381 | 0.520 |

[a]A two-tailed Student's t-test was used to compare the statistical significance of the differences in mRNA levels of control mucosa and tumor.

Comparison of mRNA Levels in Brush Cytology and Tissue Biopsy Samples

It was then tested whether tumor-associated changes in the level of a specific mRNA in brush cytology samples would also be observed in RNA from tissue biopsies from the same animals. One week after the last cytologic sample was taken, the animals were killed and tissue from tumor and normal areas was taken by dissection to produce a tissue biopsy sample. To allow a comparison of RNA from all four sample types, RNA quantities were normalized to internal standards, PPIA, and BACT. An average for the three brush cytology samples is represented in the bar graph and is plotted next to the value obtained from the RNA from surgically biopsied tissue from the same animal (FIGS. 8A-8F). Surprisingly, the results were to some degree dependent on the sampling method. First, we note that there was minimal correlation between relative mRNA levels in brush cytology samples and surgical biopsy samples from the same animal (FIGS. 8A-8F 3). Secondly, in the same figure it is demonstrated that the levels of specific mRNAs depend on the sample type. Thirdly, only one of six genes, CYP1B1 showed a change in expression with tumor formation in the surgically excised tissue (Table 1). Specifically, CYP1B1 showed increased expression in the early timepoints and decreased expression in the later timepoints. In contrast, CYP1B1 and two other genes showed changes in the brush cytology samples with tumor formation. Brush cytology mRNA quantitation was reproducible but different from tissue biopsy mRNA. One simple explanation would be that brush cytology RNA was derived from different cells than that of the tissue biopsy RNA.

Brush Cytology Sample RNA Was Highly Enriched for Epithelial Markers

To determine the identity and purity of brush cytology cells we subjected normal tissue sections to immunofluorescence analysis of epithelial cytokeratins. A control experiment showed high levels of expression in the epithelium but not in the dermis (located below the basement membrane) of an immunostained section of biopsied tissue (FIG. 9A). In the brush cytology sample over 95% of cells contained high levels of these proteins (FIG. 9B). Further, RNA from five different brush cytology samples from control hamsters was compared to RNA from tissue biopsy samples from the same hamsters. In the brush cytology sample RNA epithelial cell markers, E-cadherin and connexin-26 (CADH1 and CX26), were enriched, while desmin (DES), a muscle cell marker, and vimentin (VIM), a marker for mesenchymally derived cells, were depressed (FIG. 9C). This is consistent with the brush cytology sample being greatly enriched for mucosal epithelial cells compared to the tissue biopsy cells.

While the present invention has been described in terms of specific methods, structures, and devices it is understood that variations and modifications will occur to those skilled in the art upon consideration of the present invention. For example, the methods and compositions discussed herein can be utilized beyond the preparation of metallic surfaces for implants in some embodiments. As well, the features illustrated or described in connection with one embodiment can be combined with the features of other embodiments. Such modifications and variations are intended to be included within the scope of the present invention. Those skilled in the art will appreciate, or be able to ascertain using no more than routine experimentation, further features and advantages of the invention based on the above-described embodiments. Accordingly, the invention is not to be limited by what has been explicitly shown and described.

All publications and references are herein expressly incorporated by reference in their entirety. The terms "a" and "an" can be used interchangeably, and are equivalent to the phrase "one or more" as utilized in the present application. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

What is claimed is:

1. A method for detecting the likelihood that a subject has oral squamous cell carcinoma, comprising:
   obtaining a brush cytology sample from a subject,
   extracting nucleic acids from cells in the sample,
   assaying the nucleic acids for expression levels of non-degraded genes coding for production of beta-2 microgobulin (B2M) and cytochrome p450 1B1 (CYP1B1);
   comparing B2M gene to a standard and CYP1B1 gene to a second standard; and
   identifying over-expression of the B2M gene compared to the standard, together with under-expression of the CYP1B1 gene compared to the second standard as indicative of a likelihood that the subject has oral squamous cell carcinoma.

2. The method of claim 1, wherein the brush cytology sample comprises oral squamous cells.

3. The method of claim 1, wherein the step of obtaining the sample further comprises at least 20 brush strokes.

4. The method of claim 1, wherein the step of obtaining the sample further comprises 2 initial brush strokes to prime the surface, followed by at least 20 brush strokes to obtain the sample.

5. The method of claim 1, wherein the step of assaying the nucleic acids further comprises amplifying and quantifying expression of the B2M gene and the CYP1B1 gene by real time polymerase chain reaction using primers complementary to an mRNA sequence of at least 15 bases found near the 5' ends of the B2M and CYP1B1 genes.

6. A method for detecting the likelihood that a subject has oral squamous cell carcinoma, comprising detecting beta-2 microgobulin (B2M) and cytochrome p450 1B1 (CYP1B1) protein or nucleic acid expression levels in a brush cytology sample from the subject, and identifying over-expression of the B2M gene compared to a standard together with under-expression of the CYP1B1 gene compared to a second standard as indicative of a likelihood that the subject has oral squamous cell carcinoma.

7. A method for monitoring oral squamous cell neoplasia in a human subject over time, comprising:
   obtaining a brush cytology sample from a subject at a first time,
   extracting nucleic acids from cells in the sample,
   assaying said nucleic acids for the expression level of genes coding for the production of beta-2 microgobulin (B2M) and cytochrome p450 1B1 (CYP1B1), and
   repeating the steps of obtaining a sample, extracting nucleic acids and assaying for expression levels of B2M and CYP1B1 at a later time,
   wherein increased expression of the B2M gene at a later time or decreased expression of the CYP1B1 gene at a later time is indicative of progression of neoplasia.

* * * * *

SEQUENCE LISTING

<160> NUMBER OF SEQ ID NOS: 10

<210> SEQ ID NO 1
<211> LENGTH: 987
<212> TYPE: DNA
<213> ORGANISM: Homo sapiens

<400> SEQUENCE: 1

```
aatataagtg gaggcgtcgc gctggcgggc attcctgaag ctgacagcat tcgggccgag    60
atgtctcgct ccgtggcctt agctgtgctc gcgctactct ctctttctgg cctggaggct   120
atccagcgta ctccaaagat tcaggtttac tcacgtcatc cagcagagaa tggaaagtca   180
aatttcctga attgctatgt gtctgggttt catccatccg acattgaagt tgacttactg   240
aagaatggag agagaattga aaaagtggag cattcagact tgtctttcag caaggactgg   300
tctttctatc tcttgtacta cactgaattc accccccactg aaaaagatga gtatgcctgc   360
cgtgtgaacc atgtgacttt gtcacagccc aagatagtta agtgggatcg agacatgtaa   420
gcagcatcat ggaggtttga agatgccgca tttggattgg atgaattcca aattctgctt   480
gcttgctttt taatattgat atgcttatac acttacactt tatgcacaaa atgtagggtt   540
ataataatgt taacatggac atgatcttct ttataattct actttgagtg ctgtctccat   600
gtttgatgta tctgagcagg ttgctccaca ggtagctcta ggagggctgg caacttagag   660
gtggggagca gagaattctc ttatccaaca tcaacatctt ggtcagattt gaactcttca   720
atctcttgca ctcaaagctt gttaagatag ttaagcgtgc ataagttaac ttccaattta   780
catactctgc ttagaatttg ggggaaaatt tagaaatata attgacagga ttattggaaa   840
tttgttataa tgaatgaaac attttgtcat ataagattca tatttacttc ttatacattt   900
gataaagtaa ggcatggttg tggttaatct ggtttatttt tgttccacaa gttaaataaa   960
tcataaaact tgatgtgtta tctctta                                         987
```

<210> SEQ ID NO 2
<211> LENGTH: 5160
<212> TYPE: DNA
<213> ORGANISM: Homo sapiens

<400> SEQUENCE: 2

```
aaaacccgga ggagcgggat ggcgcgcttt gactctggag tgggagtggg agcgagcgct    60
tctgcgactc cagttgtgag agccgcaagg gcatgggaat tgacgccact caccgacccc   120
cagtctcaat ctcaacgctg tgaggaaacc tcgactttgc caggtcccca agggcagcgg   180
ggctcggcga gcgaggcacc cttctccgtc cccatcccaa tccaagcgct cctggcactg   240
acgacgccaa gagactcgag tgggagttaa agcttccagt gagggcagca ggtgtccagg   300
ccgggcctgc gggttcctgt tgacgtcttg ccctaggcaa aggtcccagt tccttctcgg   360
agccggctgt cccgcgccac tggaaaccgc acctccccgc agcatgggca ccagcctcag   420
cccgaacgac cctggccgc taaacccgct gtccatccag cagaccacgc tcctgctact   480
cctgtcggtg ctggccactg tgcatgtggg ccagcggctg ctgaggcaac ggaggcggca   540
gctccggtcc gcgcccccgg gccgttttgc gtggccactg atcggaaacg cggcggcggt   600
gggccaggcg gctcacctct cgttcgctcg cctggcgcgg cgctacggcg acgttttcca   660
gatccgcctg ggcagctgcc ccatagtggt gctgaatggc gagcgcgcca tccaccaggc   720
cctggtgcag cagggctcgg ccttcgccga ccggccggcc ttcgcctcct tccgtgtggt   780
```

```
gtccggcggc cgcagcatgg cttccggcca ctactcggag cactggaagg tgcagcggcg        840
cgcagcccac agcatgatgc gcaacttctt cacgcgccag ccgcgcagcc gccaagtcct        900
cgagggccac gtgctgagcg aggcgcgcga gctggtggcg ctgctggtgc gcggcagcgc        960
ggacggcgcc ttcctcgacc cgaggccgct gaccgtcgtg gccgtggcca acgtcatgag       1020
tgccgtgtgt ttcggctgcc gctacagcca cgacgacccc gagttccgtg agctgctcag       1080
ccacaacgaa gagttcgggc gcacggtggg cgcgggcagc ctggtggacg tgatgccctg       1140
gctgcagtac ttccccaacc cggtgcgcac cgttttccgc gaattcgagc agctcaaccg       1200
caacttcagc aacttcatcc tggacaagtt cttgaggcac tgcgaaagcc ttcggcccgg       1260
ggccgccccc cgcgacatga tggacgcctt tatcctctct gcggaaaaga aggcggccgg       1320
ggactcgcac ggtggtggcg cgcggctgga tttggagaac gtaccggcca ctatcactga       1380
catcttcggc gccagccagg acaccctgtc caccgcgctg cagtggctgc tcctcctctt       1440
caccaggtat cctgatgtgc agactcgagt gcaggcagaa ttggatcagg tcgtggggag       1500
ggaccgtctg ccttgtatgg gtgaccagcc caacctgccc tatgtcctgg ccttcctta        1560
tgaagccatg cgcttctcca gctttgtgcc tgtcactatt cctcatgcca ccactgccaa       1620
cacctctgtc ttgggctacc acattcccaa ggacactgtg gttttgtca accagtggtc        1680
tgtgaatcat gacccactga agtggcctaa cccggagaac tttgatccag ctcgattctt       1740
ggacaaggat ggcctcatca acaaggacct gaccagcaga gtgatgattt tttcagtggg       1800
caaaaggcgg tgcattggcg aagaactttc taagatgcag cttttttctct tcatctccat       1860
cctggctcac cagtgcgatt tcagggccaa cccaaatgag cctgcgaaaa tgaatttcag       1920
ttatggtcta accattaaac ccaagtcatt taaagtcaat gtcactctca gagagtccat       1980
ggagctcctt gatagtgctg tccaaaattt acaagccaag gaaacttgcc aataagaagc       2040
aagaggcaag ctgaaatttt agaaatattc acatcttcgg agatgaggag taaaattcag       2100
tttttttcca gttcctcttt tgtgctgctt ctcaattagc gtttaaggtg agcataaatc       2160
aactgtccat caggtgaggt gtgctccata cccagcggtt cttcatgagt agtgggctat       2220
gcaggagctt ctgggagatt tttttgagtc aaagacttaa agggcccaat gaattattat       2280
atacatactg catcttggtt atttctgaag gtagcattct ttggagttaa aatgcacata       2340
tagacacata cacccaaaca cttacaccaa actactgaat gaagcagtat tttggtaacc       2400
aggccatttt tggtgggaat ccaagattgg tctcccatat gcagaaatag acaaaaagta       2460
tattaaacaa agtttcagag tatattgttg aagagacaga gacaagtaat ttcagtgtaa       2520
agtgtgtgat tgaaggtgat aagggaaaag ataaagacca gaaattccct tttcacctttt       2580
tcaggaaaat aacttagact ctagtattta tgggtggatt tatccttttg ccttctggta       2640
tacttcctta ctttttaagga taaatcataa agtcagttgc tcaaaagaa atcaatagtt       2700
gaattagtga gtatagtggg gttccatgag ttatcatgaa ttttaaagta tgcattatta       2760
aattgtaaaa ctccaaggtg atgttgtacc tcttttgctt gccaaagtac agaatttgaa       2820
ttatcagcaa agaaaaaaaa aaagccagc caagctttaa attatgtgac cataatgtac       2880
tgatttcagt aagtctcata ggttaaaaaa aaaagtcacc aaatagtgtg aaatatatta       2940
cttaactgtc cgtaagcagt atattagtat tatcttgttc aggaaaaggt tgaataatat       3000
atgccttgta taatattgaa aattgaaaag tacaactaac gcaaccaagt gtgctaaaaa       3060
tgagcttgat taaatcaacc acctattttt gacatggaaa tgaagcaggg tttcttttct       3120
tcactcaaat tttggcgaat ctcaaaatta gatcctaaga tgtgttctta tttttataac       3180
```

```
                                          -continued
atctttattg aaattctatt tataatacag aatcttgttt tgaaaataac ctaattaata    3240
tattaaaatt ccaaattcat ggcatgctta aatttaact aaattttaaa gccattctga    3300
ttattgagtt ccagttgaag ttagtggaaa tctgaacatt ctcctgtgga aggcagagaa    3360
atctaagctg tgtctgccca atgaataatg gaaaatgcca tgaattacct ggatgttctt    3420
tttacgaggt gacaagagtt ggggacagaa ctcccattac aactgaccaa gtttctcttc    3480
tagatgattt tttgaaagtt aacattaatg cctgcttttt ggaaagtcag aatcagaaga    3540
tagtcttgga agctgtttgg aaaagacagt ggagatgagg tcagttgtgt tttttaagat    3600
ggcaattact ttggtagctg ggaaagcata aagctcaaat gaaatgtatg cattcacatt    3660
tagaaaagtg aattgaagtt tcaagtttta aagttcattg caattaaact tccaaagaaa    3720
gttctacagt gtcctaagtg ctaagtgctt attacattt attaagcttt ttggaatctt    3780
tgtaccaaaa ttttaaaaaa gggagttttt gatagttgtg tgtatgtgtg tgtggggtgg    3840
ggggatggta agagaaaaga gagaaacact gaaaagaagg aaagatggtt aaacattttc    3900
ccactcattc tgaattaatt aatttggagc acaaaattca aagcatggac atttagaaga    3960
aagatgtttg gcgtagcaga gttaaatctc aaataggcta ttaaaaaagt ctacaacata    4020
gcagatctgt tttgtggttt ggaatattaa aaaacttcat gtaattttat tttaaaattt    4080
catagctgta cttcttgaat ataaaaaatc atgccagtat ttttaaaggc attagagtca    4140
actacacaaa gcaggcttgc ccagtacatt taaattttt ggcacttgcc attccaaaat    4200
attatgcccc accaaggctg agacagtgaa tttgggctgc tgtagcctat ttttttagat    4260
tgagaaatgt gtagctgcaa aaataatcat gaaccaatct ggatgcctca ttatgtcaac    4320
caggtccaga tgtgctataa tctgttttta cgtatgtagg cccagtcgtc atcagatgct    4380
tgcggcaaaa ggaaagctgt gtttatatgg aagaaagtaa ggtgcttgga gtttacctgg    4440
cttatttaat atgcttataa cctagttaaa gaaaggaaaa gaaaacaaaa acgaatgaa    4500 aataactgaa tttggaggct ggagtaatca gattactgct ttaatcagaa accctcattg    4560
tgtttctacc ggagagagaa tgtatttgct gacaaccatt aaagtcagaa gttttactcc    4620
aggttattgc aataaagtat aatgtttatt aaatgcttca tttgtatgtc aaagctttga    4680
ctctataagc aaattgcttt tttccaaaac aaaagatgt ctcaggtttg ttttgtgaat    4740
tttctaaaag ctttcatgtc ccagaactta gcctttacct gtgaagtgtt actacagcct    4800
taatattttc ctagtagatc tatattagat caaatagttg catagcagta tatgttaatt    4860 tgtgtgttt tagctgtgac acaactgtgt gattaaaagg tatactttag tagacattta    4920
taactcaagg ataccttctt atttaatctt ttcttattt tgtactttat catgaatgct    4980
tttagtgtgt gcataatagc tacagtgcat agttgtagac aaagtacatt ctggggaaac    5040
aacatttata tgtagccttt actgtttgat ataccaaatt aaaaaaaaat tgtatctcat    5100
tacttatact gggacaccat taccaaaata ataaaaatca ctttcataat cttgaaaaaa    5160
```

<210> SEQ ID NO 3
<211> LENGTH: 22
<212> TYPE: DNA
<213> ORGANISM: Artificial
<220> FEATURE:
<223> OTHER INFORMATION: Forward primer sequence for hamster,
      Mesocricetus auratus, beta-2 microglobulin

<400> SEQUENCE: 3
agtttgtacc cactgcgact ga                                              22

```
<210> SEQ ID NO 4
<211> LENGTH: 22
<212> TYPE: DNA
<213> ORGANISM: Artificial
<220> FEATURE:
<223> OTHER INFORMATION: reverse primer sequence for hamster,
      Mesocricetus auratus, beta-2 microglobulin

<400> SEQUENCE: 4
tgctgctgtg tgcatagact ga                                              22

<210> SEQ ID NO 5
<211> LENGTH: 23
<212> TYPE: DNA
<213> ORGANISM: Artificial
<220> FEATURE:
<223> OTHER INFORMATION: Forward primer sequence for human, Homo sapien,
      beta-2 microglobulin

<400> SEQUENCE: 5
tgtgctcgcg ctactctctc ttt                                             23

<210> SEQ ID NO 6
<211> LENGTH: 24
<212> TYPE: DNA
<213> ORGANISM: Artificial
<220> FEATURE:
<223> OTHER INFORMATION: reverse primer sequence for human, Homo sapien,
      beta-2 microglobulin

<400> SEQUENCE: 6
atgtcggatg gatgaaaccc agac                                            24

<210> SEQ ID NO 7
<211> LENGTH: 24
<212> TYPE: DNA
<213> ORGANISM: Artificial
<220> FEATURE:
<223> OTHER INFORMATION: forward primer sequence for hamster,
      Mesocricetus auratus, Cytochrome p450 1B1

<400> SEQUENCE: 7
gaatccatgc gcttctccag cttt                                            24

<210> SEQ ID NO 8
<211> LENGTH: 24
<212> TYPE: DNA
<213> ORGANISM: Artificial Sequence
<220> FEATURE:
<223> OTHER INFORMATION: reverse primer sequence for hamster,
      Mesocricetus auratus, Cytochrome p450 1B1

<400> SEQUENCE: 8
tccaggaatc gggctggatc aaat                                            24

<210> SEQ ID NO 9
<211> LENGTH: 24
<212> TYPE: DNA
<213> ORGANISM: Artificial
<220> FEATURE:
<223> OTHER INFORMATION: forward primer sequence for human, Homo sapien,
      Cytochrome p450 1B1

<400> SEQUENCE: 9
gcctcattat gtcaaccagg tcca                                            24

<210> SEQ ID NO 10
<211> LENGTH: 24
```

```
<212> TYPE: DNA
<213> ORGANISM: Artificial
<220> FEATURE:
<223> OTHER INFORMATION: reverse primer sequence for human, Homo sapien,
      Cytochrome p450 1B1

<400> SEQUENCE: 10
aagccaggta aactccaagc acct                                              24
```